(12) United States Patent
Heredia et al.

(10) Patent No.: US 11,898,201 B2
(45) Date of Patent: *Feb. 13, 2024

(54) SPLIT-CYCLE AND TAPE AMPLIFICATION

(71) Applicant: Bio-Rad Laboratories, Inc., Hercules, CA (US)

(72) Inventors: Nicholas Heredia, Mountain House, CA (US); Dianna Maar, Mountain House, CA (US)

(73) Assignee: Bio-Rad Laboratories, Inc., Hercules, CA (US)

( * ) Notice: Subject to any disclaimer, the term of this patent is extended or adjusted under 35 U.S.C. 154(b) by 393 days.

This patent is subject to a terminal disclaimer.

(21) Appl. No.: 17/148,440

(22) Filed: Jan. 13, 2021

(65) Prior Publication Data

US 2021/0207208 A1  Jul. 8, 2021

Related U.S. Application Data

(60) Continuation of application No. 16/361,704, filed on Mar. 22, 2019, now Pat. No. 10,920,270, which is a
(Continued)

(51) Int. Cl.
| C12Q 1/68 | (2018.01) |
| C12Q 1/6865 | (2018.01) |
| C12Q 1/6816 | (2018.01) |
| C12Q 1/6858 | (2018.01) |
| C12Q 1/6827 | (2018.01) |
| C12Q 1/6848 | (2018.01) |

(Continued)

(52) U.S. Cl.
CPC ........ C12Q 1/6865 (2013.01); C12Q 1/6816 (2013.01); C12Q 1/6827 (2013.01); C12Q 1/6848 (2013.01); C12Q 1/6851 (2013.01); C12Q 1/6853 (2013.01); C12Q 1/6858 (2013.01)

(58) Field of Classification Search
CPC .. C12Q 1/6865; C12Q 1/6816; C12Q 1/6827; C12Q 1/6848; C12Q 1/6851; C12Q 1/6853; C12Q 1/6858; C12Q 2525/161
See application file for complete search history.

(56) References Cited

U.S. PATENT DOCUMENTS 10,280,455 B2 * 5/2019 Heredia ............... C12Q 1/6851
2005/0164219 A1 7/2005 Whitcombe et al.
(Continued)

FOREIGN PATENT DOCUMENTS

| WO | 032510 A1 | 3/2012 |
| WO | 110528 A1 | 7/2014 |
| WO | 179339 A1 | 11/2015 |

OTHER PUBLICATIONS

The International Search Report and Written Opinion from Application No. PCT/US2016-069009, dated Apr. 13, 2017.
(Continued)

Primary Examiner — Stephanie K Mummert
(74) Attorney, Agent, or Firm — Kilpatrick Townsend and Stockton LLP

(57) ABSTRACT

Methods and compositions are provided for improved nucleic acid amplification assays. In some embodiments, the nucleic acid amplification assay is a tagged amplicon primer extension (TAPE) nucleic acid amplification reaction.

9 Claims, 6 Drawing Sheets

Specification includes a Sequence Listing.

Related U.S. Application Data division of application No. 15/393,103, filed on Dec. 28, 2016, now Pat. No. 10,280,455.

(60) Provisional application No. 62/273,210, filed on Dec. 30, 2015.

(51) Int. Cl.
  *C12Q 1/6851* (2018.01)
  *C12Q 1/6853* (2018.01)

(56) References Cited

U.S. PATENT DOCUMENTS

| | | | |
|---|---|---|---|
| 2006/0057561 A1* | 3/2006 | Hart | C12Q 1/70 435/5 |
| 2006/0078561 A1 | 4/2006 | Sharon | |
| 2010/0221702 A1* | 9/2010 | Moser | C12Q 1/6858 435/5 |
| 2014/0220569 A1 | 8/2014 | Litterst et al. | |
| 2014/0274786 A1 | 9/2014 | McCoy et al. | |
| 2014/0309128 A1 | 10/2014 | Regan et al. | |
| 2016/0304936 A1* | 10/2016 | Ji | C12Q 1/6876 |

OTHER PUBLICATIONS

Partial Supplementary European Search Report from EP Application 16882604.8, dated Jul. 3, 2019; 18 pages.

Harismendy, O. et al.; "Detection of low prevalence somatic mutations in solid tumors with ultra-deep targeted sequencing"; Genome Biology; vol. 12, No. 2; Dec. 20, 2011; Biomed Central Ltd., London, GB; 13 pages.

Raindance Technologies, Inc.; "RainDance Technologies DeepSeq™ FFPE Solution" Data Sheet; "Discover rare cancer mutations in heterogeneous tumor cells using previously inaccessible samples"; Jan. 1, 2011; retrieved from the internet at http://raindancetech.com/rdt/wp-content/uploads/downloads/product-brief_deepseq.pdf; retrieved Apr. 16, 2019; 4 pages.

* cited by examiner

Target Sequence:
AGGCACTCTTGCCTAGGCCACCAGCTCCAACTACCACAAGTTTATATTCAGTCATTTCAGCAGGCCT Mutation-specific F1: 5' CTAGGAGTGGCTGGAATCATGGCACGAGATCCTCTCTCTG3' (54.5,61.7)
Mutation-specific R1: 5' CCTGATAACACTGATCTAGCCTGCTACTCCTGCTCAGTGATTTC3' (54.6,63.8)
Wild-type specific F2: 5' CAAGCAAGAAGACGGCATACGAGATGTCACGAGATCCTCTCTA3' (53.2,67.5)
Wild-type specific R2: 5' TTACTATGCCGTCGTGGCGTCAGTGATTT 3' (55,68.4)

Mutation-specific flanking F1: HEX CTAGGAGTGGCTGGAATCATGG
Mutation-specific sink F1: GATTCCAGACACTCCTAG IABkFQ
Mutation-specific flanking R1: CCTGATAACACTGATCTAGCCTCGTA Wild-type specific flanking F2: FAM CAAGCAAGAAGACGGCATACGAGATGT
Wild-type specific sink F2: GTATGCCGTATCTGCTT IABkFQ
Wild-type specific flanking R2: TTACTATGCCGTCGTGGCTCTAGATG 3' GTCTCTCCTAGAGCAC GTATACGTCGGAGAAGAGAGG 5'
5' XXXXXXXX GAGGACGAGTCACTAAACAGAGAGGATCTCGTGXXXXXXXXXXXX
CTCCTGCTCAGTGATTTC3'

3' ATCTCTCTCCTAGAGCAC GTAGCGCACAGAGAGAGG 5'
5' XXXXXXXXXXXXXC GAGGACGAGTCACTAAATAGAGAGGATCTCGTXXXXXXXXXXXXXXXXX
CTCCTGCTCAGTGATTT3'

By adjusting both Primer Tm and Concentration, unique primers
can be used to amplify mutant with different primers than wildtype
Ensuring equal resources during double positive droplet amplification

*FIG. 1*

Target Sequence:
AGGCACTCTTGCCTAGCGCCACCAGCTCCAACTACCACAAGTTTATATTCAGTCATTTCAGCAGCCT Mutation-specific F1:5' GAATCATGGCTTGTGGTAGTTGGAGC3'
Mutation-specific R1:5' CTAGCCTCGTA CTTGCCTACGCCACCAG3'
Wild-type specific F2:5' CATACCAGATGTCTTGTGGTAGTTGGAGG3'
Wild-type specific R2:5' CTGTGTAGATGGCCTACGCCACCAC Mutation-specific flanking F1:GAATCATGG
Mutation-specific flanking R1:CTAGCCTCGTA Wild-type specific flanking F2:CATACCAGATGT
Wild-type specific flanking R2:GGTGTAGATG Optional
Mutation-specific Probe : 5'FAM-TTGGAGCTGGTGGCG-IABkFQ3'
Wild-type specific Probe: 5'HEX-GTAGTTGGAGGTTGGTG-IABkFQ3'

5' AGGCACTCTTGCCTAGCGCCACCAGCTCCAACTACCACAAGTTTATATTCAGTCATTTCAGCAGCCT
                        CTAGCCTCGTA                    3'CGAGGTTGATGGTGTTC CGTACCGTC
              CTAGCCTCGT                                   CTTGCCTACGCCACCAG3'
                                                 IABkFQ-3'GCCGGTGGTCGAGGTT-FAM-5'

5' AGGCACTCTTGCCTAGCGCCACCAGCTCCAACTACCACAAGTTTATATTCAGTCATTTCAGCAGCCT
                                                 3'CGAGGTTGATGGTGTTC TGTAGATGATCC
                        TGTCTGTATC                                 GCCTACGCCACCAC3'
                                                 IABkFQ-3'GTGGTGGAGGTTGATG-HEX-5'

*FIG. 2*

(5'-tailed Forward Primer)F1: 5' CCTGATAACACTGATCTAGCCTCGTACTTGCCTACGC
(5'-tailed Reverse Primer)R1: 5' GTACGAGGCTAGATCAGTTATTAGGCTTGTGTAGT
Wildtype Probe: HEX-CACCAGCTCCAACTACC-BHQ Target Sequence example A wildtype only:
5' AGGCACTCTTGCCTACGCCACCAGCTCCAACTACCACAAGTTTATATTCAGTCATTTTCAGCAGGCCT 3'
3' TCCGTGAGAACGGATGCGGTGGTCGAGGTTGATGGTGTTCAAATATAAGTCAGTAAAAGTCGTCCGGA 5'

Step 1:
F1-5' CCTGATAACACTGATCTAGCCTCGTACTTGCCTACGC3'
3' TGCCTGAGAACGGATGCGGTGGTCGAGGTTGATGGTGTTCAAATATAAGTCAGTAAAAGTCGTCCGGA 5'
HEX-CACCAGCTCCAACTACC-BHQ Step 2:
TGATGGTGTTCCGGACTATTGTGACTAGATCGGAGCATG 5' R1
5' CCTGATAACACTGATCTAGCCTCGTACTTGCCTACGCCACCAGCTCCAACTACCACAAGTTTATATTCAGTCATTTTCAGCAGGGCT 3'

Step 3:
3' GGACTATTGTGACTAGATCGGAGCATGATGAACGGATCCGTAGCCTCGTACTTGCCTACGC 5'
5' CCTGATAACACTGATCTAGCCTCGTACTTGCCTACGCCACCAGCTCCAACTACCACAAGTTTATATTCAGTCATTTTCAGCAGGGCT 3'
HEX-CACCAGCTCCAACTACC-BHQ 3' GGACTATTGTGACTAGATCGGAGCATGATGAACGGATCCGTAGCCTCGTACTTGCCTACGCCACCAGCTCCAACTACCACAAG CTGATAACACTGTGACTAGATCGGAGCATG 5'
5' CCTGATAACACTGATCTAGCCTCGTACTTGCCTACGCCACCAGCTCCAACTACCACAAGCTGATAACACTGTGACTAGATCGGCCTAC 3'

↓ Amplicon ends work as primers

Step 4:
5' CCTGATAACACTGATCTAGCCTCGTACTTGCCTACGCCACCAGCTCCAACTACCACAAGCTGATAACACTGTGACTAGATCGGAGCATG 3'
3' GGACTATTGTGACTAGATCGGAGCATGATGAACGGATCCGTAGCCTCGTACTTGCCTACGCCACCAGCTCCAACTACCACAAGCTGATAACACTGTGACTAGATCGGAGCATG 5'
HEX-CACCAGCTCCAACTACC-BHQ Primer Dimers can form however no extension will occur off the 3' ends:
F1' 5' CCTGATAACACTGATCTAGCCTCGTACTTGCCTACGCCACCAG
3' CGAGGTTGATGGTGTTCCGGACTATTGTGACTAGATCGGAGCATG 5' R1

*FIG. 3a*

SPLIT-CYCLE AND TAPE AMPLIFICATION

CROSS-REFERENCE TO RELATED APPLICATIONS

This application is a continuation of U.S. patent application Ser. No. 16/361,704, filed Mar. 22, 2019, which application is a divisional of U.S. patent application Ser. No. 15/393,103, filed Dec. 28, 2016, which claims priority to U.S. Provisional Application No. 62/273,210, filed Dec. 30, 2015, the contents of each of which are hereby incorporated by reference in their entireties for any and all purposes.

REFERENCE TO A SEQUENCE LISTING

The Sequence Listing written in file SequenceListing_094868-1232716-111030US.txt created on Jan. 13, 2021, 8,084 bytes, machine format IBM-PC, MS-Windows operating system, is hereby incorporated by reference in its entirety for all purposes.

BACKGROUND OF THE INVENTION

Quantitative detection of target sequences (e.g., alleles, polymorphisms, etc.) in a nucleic acid sample is useful in a variety of contexts. For example, detection of rare target sequences can be useful for early, benign, or malignant tumor detection or monitoring; prenatal diagnostics, such as non-invasive fetal diagnostics; detection of viral or bacterial infection; environmental monitoring, and the like. In some cases, such detection requires a high level of sensitivity, accuracy, and precision in order to detect low abundance target sequences in a background of highly abundant non-target sequences.

BRIEF SUMMARY OF THE INVENTION

Described herein are methods and compositions for quantitative detection of sequences in a nucleic acid sample. The methods typically involve partitioning of a nucleic acid sample into a large number of mixture partitions in discrete reaction chambers (e.g., wells, channels, droplets, etc.). In one aspect, the partitioned sample is analyzed with in a split-cycle assay in which a pair of allele-specific amplification primers having a relatively low annealing temperature are used to append a high-temperature primer binding site to the target sequence in an initial set of nucleic acid amplification cycles. The initial set of nucleic acid amplification cycles include a low temperature annealing step. In subsequent nucleic acid amplification cycles, a pair of flanking amplification primers that hybridize to the high-temperature primer binding site provide high fidelity and highly specific amplification. The subsequent set of nucleic acid amplification cycles include a higher temperature annealing step.

In another aspect, the partitioned sample is analyzed with in a split-cycle assay in which a pair of allele-specific amplification primers having a relatively high annealing temperature are used to append a low-temperature primer binding site to the target sequence in an initial set of nucleic acid amplification cycles. The initial set of nucleic acid amplification cycles include a relatively high temperature annealing step. In subsequent nucleic acid amplification cycles, a pair of flanking amplification primers that hybridize to the low-temperature primer binding site provide high fidelity and highly specific amplification. The subsequent set of nucleic acid amplification cycles include a relatively lower temperature annealing step.

In another aspect, the partitioned sample is analyzed in a Tagged Amplicon Primer Extension (TAPE) reaction. In a TAPE reaction, target sequences are amplified using a pair of amplification primers, one 5'-tailed forward primer and one 5'-tailed reverse primer. The tails of the 5'-tailed forward and reverse primers are reverse complements of each other. The amplification reaction therefore generates amplicons that incorporate the tags (i.e., tagged amplicons). The resulting tagged amplicons have 3' ends that are reverse complements each other, and therefore work as primers. Thus, the reaction self-generates primers, preventing primer depletion during the amplification reaction. In some embodiments, TAPE primers can be used in a split-cycle assay that further includes flanking primers configured to hybridize to the amplicon tags.

In another aspect, the present invention provides a plurality of mixture partitions, the individual mixture partitions comprising: i) a mutation-specific 5'-tailed primer pair, wherein the mutation-specific 5'-tailed primer pair hybridizes to and specifically amplifies target DNA template molecules from a nucleic acid sample that comprise a mutant target sequence, if present, wherein the primers of the mutation specific 5'-tailed primer pair comprise: a) a 3' hybridization region of at least 10 nucleotides in length and less than 30 nucleotides in length that specifically hybridizes to the mutant target sequence; and b) a mutation-specific 5' tail region of at least 10 nucleotides in length and no more than 30 nucleotides in length that does not hybridize to any nucleic acid fragments in the nucleic acid sample; ii) a wild-type specific 5'-tailed primer pair, wherein the wild-type specific 5'-tailed primer pair hybridizes to and specifically amplifies target DNA template molecules comprising a wild-type target sequence, if present, wherein the primers of the wild-type specific 5'-tailed primer pair comprise: a) a 3' hybridization region of at least 10 nucleotides in length and less than 30 nucleotides in length that specifically hybridizes to the wild-type target sequence; and b) a wild-type specific 5' tail region of at least 10 nucleotides in length and no more than 30 nucleotides that does not hybridize to any nucleic acid fragments in the nucleic acid sample, wherein the wild-type specific 5' tail region is a different sequence than the mutation-specific 5' tail region; and iii) a mutation specific flanking primer pair, wherein the mutation specific flanking primer pair hybridizes to and specifically amplifies amplicons comprising the 5' tail regions of the mutation specific 5'-tailed primer pair, if present; iv) a wild-type specific flanking primer pair, wherein the wild-type specific flanking primer pair hybridizes to and specifically amplifies amplicons comprising the 5' tail regions of the wild-type specific 5'-tailed primer pair, if present; and v) a thermostable polymerase, wherein at least about 1-10 of the mixture partitions of the plurality of mixture partitions contains a target DNA template molecule that comprises a wild-type or mutant target sequence; and at least about 3-10 of the mixture partitions of the plurality of mixture partitions do not contain the target DNA template molecule.

In another aspect, the present invention provides a method for quantitating a frequency of wild-type and mutant target nucleic acid fragments in a nucleic acid sample, the method comprising: A) forming a plurality of mixture partitions of any one of the preceding claims; B) incubating the mixture partitions under thermal cycling conditions suitable for amplification of the target DNA template molecules by a polymerase chain reaction, wherein the thermal cycling conditions comprise a first set of temperature cycles and a second set of temperature cycles, wherein the second set of temperature cycles comprises an annealing temperature that is at least 5° C. higher or lower than an annealing temperature of the first set of temperature cycles; C) detecting the presence or absence of amplified target DNA template in the mixture partitions, wherein the detecting comprises, thereby determining: i) a number of wild-type mixture partitions comprising amplified target DNA template consisting of wild-type target sequence; ii) a number of mutant mixture partitions comprising amplified target DNA template consisting of mutant target sequence; and iii) a number of double-positive mixture partitions comprising amplified target DNA comprising mutant and wild-type target sequence; and D) determining from the number of wild-type, mutant, and double-positive mixture partitions the frequency of wild-type and mutant target nucleic acid fragments in the nucleic acid sample.

In another aspect, the present invention provides a reaction mixture for performing a tagged amplicon primer extension (TAPE) nucleic acid amplification reaction, the mixture comprising: i) a target DNA template molecule from a nucleic acid sample, wherein the target DNA template molecule comprises a target sequence; ii) a forward primer comprising: a) a 3' hybridization region of at least 10 nucleotides in length and no more than 30 nucleotides in length that is configured to specifically hybridize to the target sequence of the target DNA template molecule and generate a first primer extension product in the nucleic acid amplification reaction; and b) a 5' tail region of at least 10 nucleotides in length that is not complementary to the target sequence of the target DNA template molecule; iii) a reverse primer comprising: a) a 3' hybridization region of at least 10 nucleotides in length and no more than 30 nucleotides in length that is configured to specifically hybridize to the first primer extension product and generate a second primer extension product in in the nucleic acid amplification reaction; and b) a tail region of at least 10 nucleotides in length that is not complementary to the target sequence of the target DNA template molecule, wherein the 5' tail region of the reverse primer is a reverse complement of the 5' tail region of the forward primer; and iv) a thermostable polymerase.

In another aspect, the present invention provides a plurality of mixture partitions, the individual mixture partitions comprising any one of the foregoing reaction mixtures.

In another aspect, the present invention provides a method for performing a tagged amplicon primer extension (TAPE) nucleic acid amplification reaction, the method comprising: i) forming any one of the foregoing reaction mixtures, or any one of the foregoing pluralities of reaction mixtures; ii) hybridizing a forward primer to a target sequence of a target DNA template molecule; iii) extending the hybridized forward primer with a polymerase, thereby generating a first primer extension product; iv) hybridizing a reverse primer to the first primer extension product; v) extending the hybridized reverse primer with the polymerase, thereby generating a second primer extension product; vi) hybridizing the forward primer to the second primer extension product; v) extending the forward primer hybridized to the second primer extension product with the polymerase, thereby generating a third primer extension product, wherein the second and third primer extension products form a first double-stranded amplicon, wherein the first double-stranded amplicon comprises two complementary strands having 3' and 5' ends, wherein the 3' ends are reverse complements of each other, and the 5' ends are reverse complements of each other.

In another aspect, the present invention provides a method for performing a tagged amplicon primer extension (TAPE) nucleic acid amplification reaction, the method comprising: i) forming any one of the foregoing reaction mixtures; ii) hybridizing: a) a mutant-specific forward primer to a mutant target sequence of a target DNA template molecule, if present; and b) a wild-type specific forward primer to a wild-type target sequence of a target DNA template molecule; iii) extending the hybridized forward primer(s) with a polymerase, thereby generating a mutant first primer extension product if the mutant target sequence is present and a wild-type first primer extension product; iv) hybridizing: a) a mutant-specific reverse primer to the mutant first primer extension product, if present; and b) a wild-type specific reverse primer to the wild-type first primer extension product; v) extending the hybridized reverse primer(s) with the polymerase, thereby generating a mutant second primer extension product if the mutant target sequence is present, and a wild-type second primer extension product; vi) hybridizing the forward primer(s) to the second primer extension product(s), if present; v) extending the forward primer(s) hybridized to the second primer extension product(s) with the polymerase, thereby generating a mutant third primer extension product, if the mutant target sequence is present and a wild-type third primer extension product, wherein: the second and third mutant primer extension products form a mutant double-stranded amplicon, if the mutant target sequence is present, wherein the mutant double-stranded amplicon comprises two complementary strands having 3' and 5' ends, wherein the 3' ends are reverse complements of each other, and the 5' ends are reverse complements of each other; and the second and third wild-type primer extension products form a wild-type double-stranded amplicon, wherein the wild-type double-stranded amplicon comprises two complementary strands having 3' and 5' ends, wherein the 3' ends of the first wild-type double-stranded amplicon are reverse complements of each other and the 5' ends of the first wild-type double-stranded amplicon are reverse complements of each other.

In another aspect, the present invention provides A method for quantitative rare mutation detection, the method comprising: i) providing any one of the foregoing pluralities of mixture partitions; ii) performing a split-cycle assay, TAPE assay, or combination thereof to separately detect wild-type and mutant target DNA template molecules in the plurality of mixture partitions, thereby detecting a number of mixture partitions that are positive for a presence of the mutant but not the wild-type target DNA template, a number of mixture partitions that are positive for a presence of the wild-type but not the mutant target DNA template, a number of mixture partitions that are positive for the presence of both the mutant and wild-type target DNA template, and a number of mixture partitions that are negative for the presence of mutant and wild-type target DNA template; and iii) determining the frequency of the mutant sequence in the nucleic acid sample from the number of single-positive, double-positive, and negative mixture partitions.

BRIEF DESCRIPTION OF THE DRAWINGS

FIG. 1: illustrates exemplary primers and probes for performing an allele-specific split-cycle assay to simultaneously detect a mutant (SEQ ID NO: 12, 13) and wild-type target sequence (SEQ ID NO: 1). In this embodiment, the assay uses a mutation-specific 5'-tailed forward primer (Mutation-specific F1 (SEQ ID NO: 2)), 5'-tailed reverse primer (Mutation-specific R1 (SEQ ID NO: 3)), fluorescently labeled flanking forward primer (Mutation-specific flanking F1 (SEQ ID NO: 6)), flanking reverse primer (Mutation-specific flanking R1 (SEQ ID NO: 8)), and sink oligonucleotide (Mutant-specific sink (SEQ ID NO: 7)), to amplify and detect mutant target sequence. The assay further uses a wild-type specific 5'-tailed forward primer (Wild-type specific F2 (SEQ ID NO: 4)), 5'-tailed reverse primer (Wild-type specific R2 (SEQ ID NO: 5)), fluorescently labeled flanking forward primer (Wild-type specific flanking F2 (SEQ ID NO: 9)), flanking reverse primer (Wild-type specific flanking R2 (SEQ ID NO: 11)), and sink oligonucleotide (Wild-type specific sink (SEQ ID NO: 10)), to amplify and detect wild-type target sequence. FAM and HEX refer to differentially detectable fluorescein derivatives. IABkFQ refers to an Iowa Black fluorophore quencher. In this embodiment, the flanking primers have a higher annealing temperature than the 5'-tailed primers, and the split-cycle assay would include a first set of temperature cycles having an annealing temperature and a second set of temperature cycles having an annealing temperature that is higher than the second set. In some embodiments, a different probe chemistry, such as an hydrolysis probe or an intercalating dye, can be used in addition or in the alternative to nucleic acid probes.

FIG. 2: illustrates exemplary primers and probes for performing an allele-specific split-cycle assay to simultaneously detect a mutant (SEQ ID NO: 24) and wild-type target sequence (SEQ ID NO: 1). In this embodiment, the assay uses a mutation-specific 5'-tailed forward primer (Mutation-specific F1 (SEQ ID NO: 14)), 5'-tailed reverse primer (Mutation-specific R1(SEQ ID NO: 15)), flanking forward primer (Mutation-specific flanking F1 (SEQ ID NO: 18)), flanking reverse primer (Mutation-specific flanking R1 (SEQ ID NO: 19)), and probe (Mutant-specific Probe), to amplify and detect mutant target sequence. The assay further uses a wild-type specific 5'-tailed forward primer (Wild-type specific F2 (SEQ ID NO: 16)), 5'-tailed reverse primer (Wild-type specific R2 (SEQ ID NO: 17)), flanking forward primer (Wild-type specific flanking F2 (SEQ ID NO: 20)), flanking reverse primer (Wild-type specific flanking R2 (SEQ ID NO: 21)), and probe (Wild-type specific Probe (SEQ ID NO: 23), Mutation-specific Probe (SEQ ID NO: 22)), to amplify and detect wild-type target sequence. FAM and HEX refer to differentially detectable fluorescein derivatives. IABkFQ3' refers to an Iowa Black fluorophore quencher. In this embodiment, the flanking primers have a lower annealing temperature than the 5'-tailed primers, and the split-cycle assay would include a first set of temperature cycles having an annealing temperature and a second set of temperature cycles having an annealing temperature that is lower than the second set. In some embodiments, a different probe chemistry, such as a fluorescently labeled flanking primer and short complementary quencher as in FIG. 1, or an intercalating dye, can be used in addition or in the alternative to nucleic acid probes.

FIGS. 3a-3b: illustrates exemplary primers and amplification reactions for performing a TAPE assay. (a) In this embodiment, the assay uses a 5'-tailed forward primer (F1) (SEQ ID NO: 25) and 5'-tailed reverse primer (R1) (SEQ ID NO: 26) to amplify a target sequence (SEQ ID NO: 1, 28). An hydrolysis probe (Wild-type Probe (SEQ ID NO: 27)) labeled with the HEX fluorophore and a blackhole quencher (BHQ) is used to detect amplification (e.g., step 3) and amplicons (e.g., step 4). In step 1, primer F1 hybridizes to a target strand (SEQ ID NO: 28) of the target double-stranded DNA molecule (SEQ ID NO: 28), and a polymerase reaction extends the primer. In step 2, primer R1 (SEQ ID NO: 29) hybridizes to the extended F1 primer (SEQ ID NO: 30) and a polymerase reaction extends the primer. In step 3, primer F1 hybridizes to the extended R1 primer (SEQ ID NO: 31) and a polymerase reaction extends the primer, thereby generating a tagged double-stranded amplicon having 3' ends that are reverse complements of each other (SEQ ID NO: 31, 32). Step 4 illustrates use of the strands of the tagged amplicon (SEQ ID NO: 27) as primers to generate an second tagged amplicon having 3' ends that are reverse complements of each other. The strands of the second tagged amplicon can also function as primers, and further amplification cycles can generate further tagged amplicons having 3' ends that are reverse complements of each other and function as primers (SEQ ID NO: 33, 34). In this example, 3' to 5' exonuclease activity in the reaction mixture degrades the 3' ends of the target molecule, but 3' to 5' exonuclease activity is not an essential element of all TAPE reactions described herein.

(b) In this embodiment, the assay uses a 5'-tailed forward primer (F1) (SEQ ID NO: 33) and 5'-tailed reverse primer (R1) (SEQ ID NO: 36) to amplify a target sequence. One 5'-tailed primer is labeled with a fluorophore (FAM). The assay further includes a black hole quencher (BHQ)-labeled sink oligonucleotide (Sink) (SEQ ID NO: 35) that is complementary to the 5' end of the labeled primer to detect amplification. In step 1, primer F1 (SEQ ID NO: 33) hybridizes to a target strand of the target double-stranded DNA molecule (SEQ ID NO: 28), and a polymerase extends the primer. In step 2, primer R1 (SEQ ID NO: 34) hybridizes to the extended F1 primer (SEQ ID NO: 30) and a polymerase reaction extends the primer. In step 3, primer F1 (SEQ ID NO: 33) hybridizes to the extended R1 primer (SEQ ID NO: 31) and a polymerase reaction extends the primer, thereby generating a tagged double-stranded amplicon having 3' ends that are reverse complements of each other (SEQ ID NO: 31, 32). Step 4 illustrates use of the strands of the tagged amplicon as primers to generate an second tagged amplicon having 3' ends that are reverse complements of each other (SEQ ID NO: 31, 32). The strands of the second tagged amplicon can also function as primers (SEQ ID NO: 33, 34), and further amplification cycles can generate further tagged amplicons having 3' ends that are reverse complements of each other and function as primers. In this example, 3' to 5' exonuclease activity in the reaction mixture degrades the 3' ends of the target molecule, but 3' to exonuclease activity is not an essential element of all TAPE reactions described herein.

Figure 4:
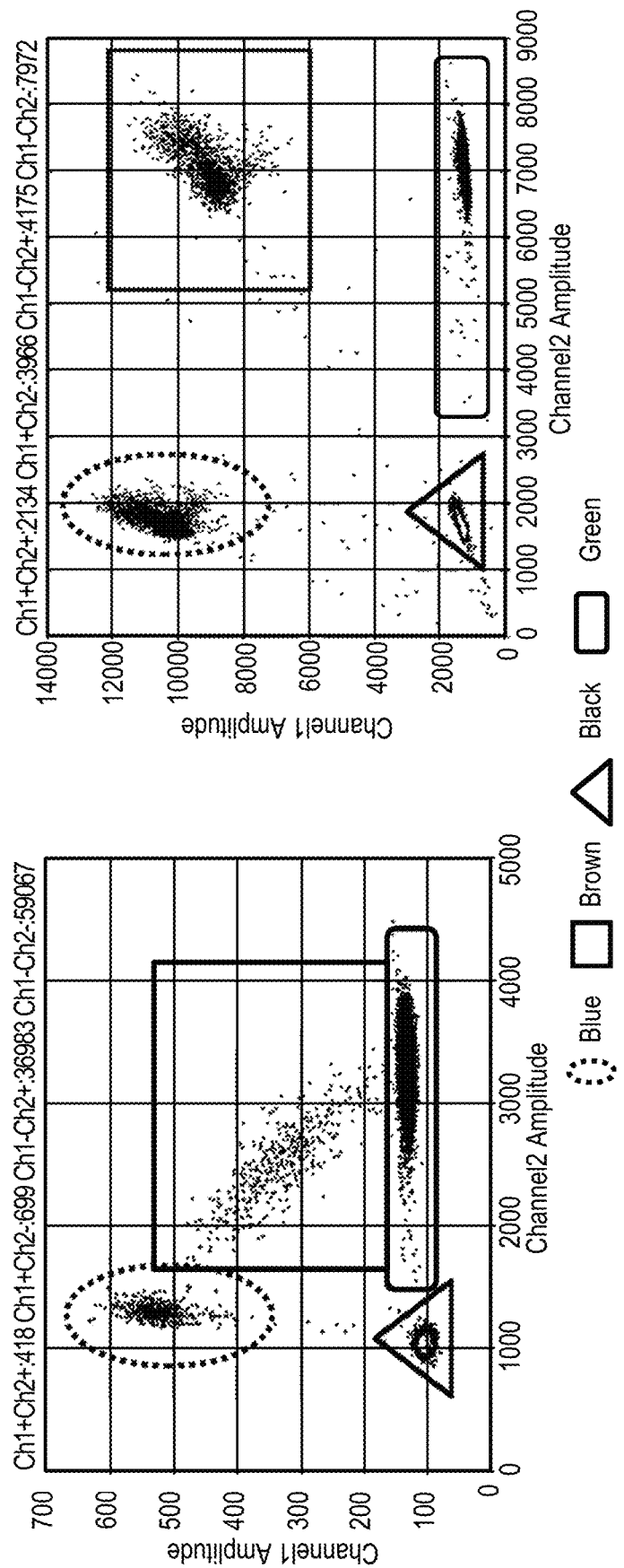

FIG. 4: illustrates a comparison between typical results of a rare mutation detection assay using conventional droplet digital amplification methods (Left) and a split-cycle, TAPE, or split-cycle and TAPE assay (Right). Channel 1 represents a detection signal from a mutant-specific hydrolysis probe. Channel 2 represents the signal from a wild-type specific hydrolysis probe. In the conventional assay, primer depletion and competition result in double-positive droplets that smear into the wild-type and/or mutant only (single-positive) detection regions, decreasing the accuracy of the assay. In comparison, methods described herein result well-separated single- and double-positive regions.

Figure 5:
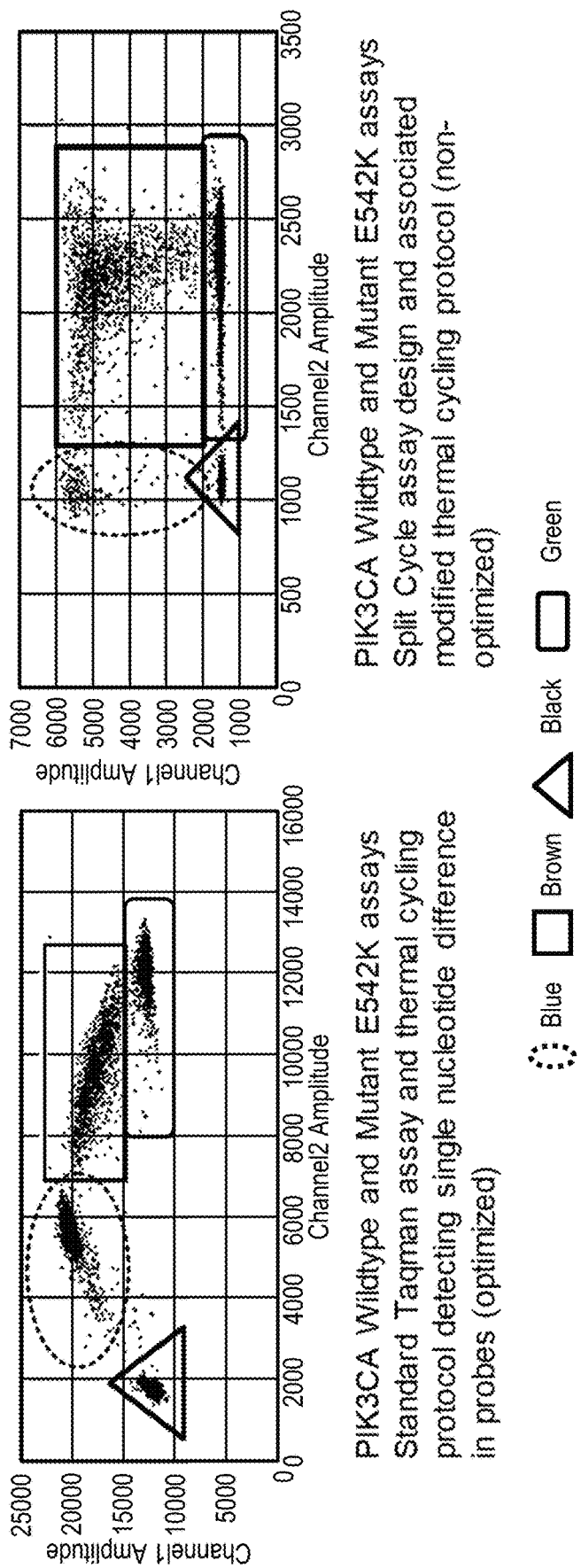

FIG. 5: illustrates exemplified data from a split-cycle droplet digital PCR assay performed using methods described herein for rare mutation detection. (Left) As a control, PIK3CA wild-type and mutant E542K assays using a standard PCR amplification protocol with Taqman detection to differentially detect the single nucleotide polymorphism were performed. Channel 1 represents a detection signal from a mutant-specific hydrolysis probe. Channel 2 represents the signal from a wild-type specific hydrolysis probe. In the conventional assay, primer depletion and competition resulted in double-positive droplets that smeared into the wild-type and/or mutant only (single-positive) detection regions, decreasing the accuracy of the assay. In comparison, split-cycle methods described herein resulted in well-separated single- and double-positive regions.

DEFINITIONS

Unless defined otherwise, technical and scientific terms used herein have the same meaning as commonly understood by a person of ordinary skill in the art. See, e.g., Lackie, DICTIONARY OF CELL AND MOLECULAR BIOLOGY, Elsevier (4$^{th}$ ed. 2007); Sambrook et al., MOLECULAR CLONING, A LABORATORY MANUAL, Cold Spring Harbor Lab Press (Cold Spring Harbor, NY 1989). The term "a" or "an" is intended to mean "one or more." The term "comprise," and variations thereof such as "comprises" and "comprising," when preceding the recitation of a step or an element, are intended to mean that the addition of further steps or elements is optional and not excluded. Any methods, devices and materials similar or equivalent to those described herein can be used in the practice of this invention. The following definitions are provided to facilitate understanding of certain terms used frequently herein and are not meant to limit the scope of the present disclosure.

As used herein, the term "complement" or "complementary" in reference to a primer, oligonucleotide, amplicon, or target sequence, or region of the primer, oligonucleotide, amplicon, or target sequence, can include the reverse complement or reverse complementarity as required to maintain functionality of the primer, oligonucleotide, amplicon, or target sequence or region thereof.

The term "amplification reaction" refers to any in vitro means for multiplying the copies of a target sequence of nucleic acid in a linear or exponential manner. Such methods include but are not limited to polymerase chain reaction (PCR); DNA ligase chain reaction (see U.S. Pat. Nos. 4,683,195 and 4,683,202; PCR Protocols: A Guide to Methods and Applications (Innis et al., eds, 1990)) (LCR); QBeta RNA replicase and RNA transcription-based amplification reactions (e.g., amplification that involves T7, T3, or SP6 primed RNA polymerization), such as the transcription amplification system (TAS), nucleic acid sequence based amplification (NASBA), and self-sustained sequence replication (3 SR); isothermal amplification reactions (e.g., single-primer isothermal amplification (SPIA)); as well as others known to those of skill in the art.

"Amplifying" refers to a step of submitting a solution to conditions sufficient to allow for amplification of a polynucleotide if all of the components of the reaction are intact. Components of an amplification reaction include, e.g., primers, a polynucleotide template, polymerase, nucleotides, and the like. The term "amplifying" typically refers to an "exponential" increase in target nucleic acid. However, "amplifying" as used herein can also refer to linear increases in the numbers of a select target sequence of nucleic acid, such as is obtained with cycle sequencing or linear amplification.

The term "amplification reaction mixture" refers to an aqueous solution comprising the various reagents used to amplify a target nucleic acid. These include enzymes, aqueous buffers, salts, amplification primers, target nucleic acid, and nucleoside triphosphates. Amplification reaction mixtures may also further include stabilizers and other additives to optimize efficiency and specificity. Depending upon the context, the mixture can be either a complete or incomplete amplification reaction mixture "Polymerase chain reaction" or "PCR" refers to a method whereby a specific segment or subsequence of a target double-stranded DNA, is amplified in a geometric progression. PCR is well known to those of skill in the art; see, e.g., U.S. Pat. Nos. 4,683,195 and 4,683,202; and PCR Protocols: A Guide to Methods and Applications, Innis et al., eds, 1990. Exemplary PCR reaction conditions typically comprise either two or three step cycles. Two step cycles have a denaturation step followed by a hybridization/elongation step. Three step cycles comprise a denaturation step followed by a hybridization step followed by a separate elongation step.

A "primer" refers to a polynucleotide sequence that hybridizes to a sequence on a target nucleic acid and serves as a point of initiation of nucleic acid synthesis. Primers can be of a variety of lengths and are often less than 50 nucleotides in length, for example 12-30 nucleotides, in length. The length and sequences of primers for use in PCR can be designed based on principles known to those of skill in the art, see, e.g., Innis et al., supra. Primers can be DNA, RNA, or a chimera of DNA and RNA portions. In some cases, primers can include one or more modified or non-natural nucleotide bases. In some cases, primers are labeled. A "pair" of primers, "primer pair," "pair of forward and reverse primers," and the like refers to a first and second primer, wherein one primer is a "forward" primer and the second primer is a "reverse" primer configured to hybridize to a target sequence and amplify the target sequence under PCR amplification conditions.

A nucleic acid, or a portion thereof, "hybridizes" to another nucleic acid under conditions such that non-specific hybridization is minimal at a defined temperature in a physiological buffer (e.g., pH 6-9, 25-150 mM chloride salt). In some cases, a nucleic acid, or portion thereof, hybridizes to a conserved sequence shared among a group of target nucleic acids. In some cases, a primer, or portion thereof, can hybridize to a primer binding site if there are at least about 6, 7, 8, 9, 10, 11, 12, 13, 14, 15, 16, 17, or 18 contiguous complementary nucleotides, including "universal" nucleotides that are complementary to more than one nucleotide partner. Alternatively, a primer, or portion thereof, can hybridize to a primer binding site if there are fewer than 1 or 2 complementarity mismatches over at least about 12, 13, 14, 15, 16, 17, or 18 contiguous nucleotides. In some embodiments, the defined temperature at which specific hybridization occurs is room temperature. In some embodiments, the defined temperature at which specific hybridization occurs is higher than room temperature. In some embodiments, the defined temperature at which specific hybridization occurs is at least about 37, 40, 42, 45, 50, 55, 65, 70, or 75° C. In some embodiments, the defined temperature at which specific hybridization occurs is 37, 40, 42, 45, 50, 55, 60, 65, 70, or 75° C.

A "template" refers to a polynucleotide sequence that comprises the polynucleotide to be amplified, flanked by a pair of primer hybridization sites or adjacent to a primer hybridization site. Thus, a "target template" comprises the target polynucleotide sequence adjacent to at least one hybridization site for a primer. A "target DNA template" comprises a target DNA polynucleotide sequence. In some cases, a "target template" comprises the target polynucleotide sequence flanked by a hybridization site for a "forward" primer and a "reverse" primer. A target template molecule, such as a target DNA template molecule, can comprise a mutant sequence or a wild-type sequence. A plurality of target DNA template molecules can comprise a plurality of wild-type sequences, a plurality of mutant sequences, or a combination thereof.

As used herein, "nucleic acid" means DNA, RNA, single-stranded, double-stranded, or more highly aggregated hybridization motifs, and any chemical modifications thereof. Modifications include, but are not limited to, those providing chemical groups that incorporate additional charge, polarizability, hydrogen bonding, electrostatic interaction, points of attachment and functionality to the nucleic acid ligand bases or to the nucleic acid ligand as a whole. Such modifications include, but are not limited to, peptide nucleic acids (PNAs), phosphodiester group modifications (e.g., phosphorothioates, methylphosphonates), 2'-position sugar modifications, 5-position pyrimidine modifications, 8-position purine modifications, modifications at exocyclic amines, substitution of 4-thiouridine, substitution of 5-bromo or 5-iodo-uracil; backbone modifications, methylations, unusual base-pairing combinations such as the isobases, isocytidine and isoguanidine and the like. Nucleic acids can also include non-natural bases, such as, for example, nitroindole. Modifications can also include 3' and 5' modifications including but not limited to capping with a fluorophore (e.g., quantum dot or fluorescent organic dye) or another moiety.

"Probe" refers to an oligonucleotide which binds through complementary base pairing to a subsequence of a target nucleic acid. It will be understood by one of skill in the art that probes will typically substantially bind target sequences lacking complete complementarity with the probe sequence depending upon the stringency of the hybridization conditions. The probes are typically directly labeled (e.g., with isotopes or fluorescent moieties) or indirectly labeled such as with digoxigenin or biotin. In some cases, the probe is a detectably labeled primer. By assaying for the presence or absence of the probe, and/or its detectable label, one can detect the presence or absence of the target. In some cases, the probe binds target sequences having complete complementary with the probe, but does not bind targets that differ from the target sequence by a single nucleotide or more.

"Sink oligonucleotide" refers to a short oligonucleotide that is complementary to a probe or primer that is detectably labeled with a photoluminophore. The sink oligonucleotide is labeled with an energy transfer partner that quenches the detectable signal of the complementary detectably labeled probe or primer when hybridized thereto. Detection of a presence or absence of an unquenched signal from the photoluminophore indicates the presence or absence respectively of a target nucleic acid. The quenching can be reduced or eliminated by degradation of the sink oligonucleotide or otherwise disrupting the hybridization complex between the sink oligonucleotide and detectably labeled primer.

As used herein, the term "partitioning" or "partitioned" refers to separating a sample into a plurality of portions, or "partitions." Partitions can be solid or fluid. In some embodiments, a partition is a solid partition, e.g., a micro channel. In some embodiments, a partition is a fluid partition, e.g., a droplet. In some embodiments, a fluid partition (e.g., a droplet) is a mixture of immiscible fluids (e.g., water and oil), or an emulsion. In some embodiments, a fluid partition (e.g., a droplet) is an aqueous droplet that is surrounded by an immiscible carrier fluid (e.g., oil). In other embodiments, a fluid partition is an aqueous droplet that is physically or chemically separated from adjacent aqueous droplets such that the contents of one droplet does not diffuse into adjacent droplets.

A "polymerase" refers to an enzyme that performs template-directed synthesis of polynucleotides, e.g., DNA and/ or RNA. The term encompasses both the full length polypeptide and a domain that has polymerase activity. DNA polymerases are well-known to those skilled in the art, including but not limited to DNA polymerases isolated or derived from *Pyrococcus furiosus, Thermococcus litoralis*, and *Thermotoga* maritime, or modified versions thereof.

Additional examples of commercially available polymerase enzymes include, but are not limited to: Klenow fragment (New England Biolabs® Inc.), Taq DNA polymerase (QIAGEN), 9° N™ DNA polymerase (New England Biolabs® Inc.), Deep Vent™ DNA polymerase (New England Biolabs® Inc.), Manta DNA polymerase (Enzymatics®), Bst DNA polymerase (New England Biolabs® Inc.), and phi29 DNA polymerase (New England Biolabs® Inc.).

Polymerases include both DNA-dependent polymerases and RNA-dependent polymerases such as reverse transcriptase. At least five families of DNA-dependent DNA polymerases are known, although most fall into families A, B and C. Other types of DNA polymerases include phage polymerases. Similarly, RNA polymerases typically include eukaryotic RNA polymerases I, II, and III, and bacterial RNA polymerases as well as phage and viral polymerases. RNA polymerases can be DNA-dependent and RNA-dependent.

The terms "label," "detectable label, "detectable moiety," and like terms refer to a composition detectable by spectroscopic, photochemical, biochemical, immunochemical, chemical, or other physical means. For example, useful labels include fluorescent dyes (fluorophores), luminescent agents, electron-dense reagents, enzymes (e.g., as commonly used in an ELISA), biotin, digoxigenin, $^{32}P$ and other isotopes, haptens, and proteins which can be made detectable, e.g., by incorporating a radiolabel into the peptide or used to detect antibodies specifically reactive with the peptide. The term includes combinations of single labeling agents, e.g., a combination of fluorophores that provides a unique detectable signature, e.g., at a particular wavelength or combination of wavelengths. Any method known in the art for conjugating label to a desired agent may be employed, e.g., using methods described in Hermanson, Bioconjugate Techniques 1996, Academic Press, Inc., San Diego.

DETAILED DESCRIPTION OF THE INVENTION

I. Overview

Described herein are methods and compositions for performing split-cycle and tagged amplicon primer extension (TAPE) amplification of nucleic acids from a sample. The split-cycle and TAPE methods are not mutually exclusive. Accordingly, described herein are methods and composition for performing split-cycle and TAPE amplification in an nucleic acid amplification reaction or a plurality of nucleic acid amplification reactions.

The methods and compositions can, e.g., reduce competition for primers between mutant and wild-type target templates in a nucleic acid amplification reaction. The methods and compositions can additionally or alternatively reduce or eliminate primer depletion in a nucleic acid amplification reaction by, e.g., generating additional primers in situ. In some cases, the methods and compositions described herein can lower the error-rate of quantitative nucleic acid amplification by lowering the number of mutations generated by the polymerase in an amplification reaction.

In some cases, the methods and compositions described herein involve quantitative analysis of multiple different target templates (e.g., two-dimensional analysis of mutant and wild-type target sequence) in a partitioned nucleic acid sample. In such cases, the methods and compositions described herein can, e.g., provide increased separation between single-positive and double-positive partitions, thus allowing easier thresholding and lowering the error rate of the analysis.

II. Compositions

Described herein are compositions for performing nucleic acid amplification reactions.

a. Split-Cycle Compositions

In one aspect, the composition is a primer or set of primers for performing a split-cycle amplification reaction. Primers for performing split-cycle amplification reactions include, but are not limited to, 5'-tailed primers and flanking primers. 5'-tailed primers are typically used in pairs of forward and reverse 5'-tailed primers to amplify an intervening target sequence of a target template. The 5'-tailed primers include a 3' hybridizing region that specifically hybridizes to the target sequence and functions as a primer in a polymerase-mediated primer extension reaction. The 3' hybridizing regions of the forward and reverse 5'-tailed primers are typically configured to hybridize to opposite strands of a target template such that the 3' ends are oriented toward each other. As such, the primers can be used to amplify the target template and produce a pair of reverse complementary primer extension products, i.e., amplicons.

The primer extension products and amplicons of such an amplification reaction include the target sequence and 5' tail sequences of the 5'-tailed primers. The 5'-tail regions of the 5'-tailed primers, corresponding primer extension products, and amplicons resulting from amplification with the 5'-tailed primers can be selected to serve as primer binding sites for flanking primers. In some cases, the 5'-tail regions are selected to comprise a pair of unique, or substantially unique, sequences as compared to the oligonucleotide sequences of the analyzed nucleic acid sample. For example, if the nucleic acid sample is a sample of nucleic acid from a human subject, the 5'-tail regions can be selected to be unique as compared to the sequence of the human genome.

In some cases, the 5'-tail regions of the 5'-tailed primers of a 5'-tailed primer pair (i.e., a forward 5'-tailed primer and corresponding reverse 5'-tailed primer) can be reverse complements of each other. In such cases, the 5'-tailed primers can support tagged amplicon primer extension (TAPE). In a TAPE reaction, the 5'-tailed primers generate amplicons that have 3' ends that serve as primers in subsequent amplification cycles. Compositions and methods for TAPE are further described herein.

Flanking primers are typically used in pairs of forward and reverse flanking primers to hybridize to the 5'-tail regions of the primer extension products and amplicons produced by amplification of the target templates with the forward and reverse 5'-tailed primer pairs. The flanking primers are configured to hybridize to opposite strands of the 5'-tailed primer extension products target template such that the 3' ends are oriented toward each other. Thus, the split-cycle amplification includes a first set of amplification cycles in which 5'-tailed forward and reverse primers hybridize to target templates and are extended to produce 5'-tailed primer extension products and amplicons, and a second set of amplification cycles in which flanking primers hybridize to the 5'-tailed primer extension products and are extended to produce amplicons.

i. 5'-Tailed Primers for Split-Cycle Up Amplification

In some embodiments, the 5'-tailed forward and 5'-tailed reverse primers anneal to the target DNA template at a relatively low temperature as compared to the annealing of the flanking primers to the products of the first set of amplification cycles. Split-cycle amplification in which the annealing temperature of the 5'-tailed primers is lower than the annealing temperature of the flanking primers is referred to as split-cycle up amplification because the annealing temperature is raised up in a second set of amplification cycles. In some cases, this difference in annealing temperatures can provide for control of whether extension of 5'-tailed primers or extension of flanking primers is predominantly performed in a reaction in a given cycle. For example, as explained in further detail below, 5'-tailed primer extension can be favored during a first set of amplification cycles having relatively low temperature annealing, and optionally primer extension, stages. Similarly, flanking primer extension can be favored during a second set of amplification cycles having relatively high temperature annealing, and optionally primer extension stages.

Thus, the hybridization regions of the 5'-tailed primers can be shorter than the hybridization regions of the flanking primers. In some embodiments, the hybridization regions of the 5'-tailed primers are at least about 8 nucleotides in length. In some cases, the hybridization regions of the 5'-tailed primers are 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, or 45 nucleotides in length. In some cases, the hybridization regions of the 5'-tailed primers are from about 8 to about 45, from about 9 to about 40, from about 8 to about 35, from about 8 to about from about 9 to about 30, from about 10 to about 30, from about 11 to about 25, from about 12 to about 25, or from about 15 to about 25 nucleotides in length. In some cases, the hybridization regions of the 5'-tailed primers are from about 8 to about 15, from about 9 to about 15, from about 10 to about 15, from about 12 to about 15, from about 8 to about 20, from about 9 to about 20, from about 10 to about 20, from about 12 to about 20, or from about 15 to about 20 nucleotides in length. In some cases, the hybridization regions of the 5'-tailed primers are from about 8 to about 25, from about 9 to about 25, from about 10 to about 25, from about 12 to about from about 15 to about 25, from about 18 to about 25, from about 8 to about 30, from about 9 to about 30, from about 10 to about 30, from about 12 to about 30, from about 15 to about 30, from about 18 to about 30, or from about 20 to about 30 nucleotides in length.

Additionally, or alternatively, the hybridization regions of the 5'-tailed primers can have a lower G-C content, or be modified to exhibit a reduce annealing temperature as compared to the flanking primers in the split-cycle reaction. In some cases, the hybridization regions of the 5'-tailed primers have an annealing temperature that is at least 1° C. lower than the lowest hybridization temperature of the flanking primers in the split-cycle reaction. In some cases, the hybridization regions of the 5'-tailed primers have an annealing temperature that is, is about, is at least, or is at least about, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, or 45° C. lower than the lowest hybridization temperature of the flanking primers in the split-cycle reaction. In some cases, the hybridization regions of the 5'-tailed primers have an annealing temperature that is from about 1° C. to about 45° C., from about 2° C. to about 35° C., from about 3° C. to about 30° C., from about 5° C. to about 20° C., from about 5° C. to about 15°

C., or from about 5° C. to about ° C. less than the lowest hybridization temperature of the flanking primers in the split-cycle reaction.

In some embodiments, the hybridization regions of the 5'-tailed primers have an annealing temperature of less than about 75° C. In some embodiments, the hybridization regions of the 5'-tailed primers have an annealing temperature of from about 30° C. to about 75° C., from about 35° C. to about 70° C.; from about 40° C. to about 65° C.; from about 45° C. to about 60° C.; or from about 45° C. to about 55° C. In some embodiments, the hybridization regions of the 5'-tailed primers have an annealing temperature of, or at least, of about, or of at least about, 35, 40, 50, 55, 60, or 65° C. (e.g., and less than about 75° C.).

The 5'-tail regions of the 5'-tailed primers can be configured to provide a primer binding site for the corresponding flanking primer that has a higher annealing temperature than the annealing temperature of the 5-tailed primers to the target DNA template. Additionally or alternatively, the 5'-tail regions can have a longer length in nucleotides than the 3' hybridization regions. In some embodiments, the 5'-tail regions of the 5'-tailed primers are at least about 10 nucleotides in length. In some cases, the 5'-tail regions of the 5'-tailed primers are, are about, are at least, or are at least about, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, or 45 nucleotides in length. In some cases, the 5'-tail regions of the 5'-tailed primers are from about 10 to about 45, from about 11 to about 40, from about 12 to about 35, from about 10 to about 30, from about 11 to about 30, from about 12 to about 30, or from about 15 to about 30 nucleotides in length. In some cases, the 5'-tail regions of the 5'-tailed primers are from about 12 to about 25, from about 15 to about 25, from about 20 to about 25, from about 12 to about 30, from about 15 to about 30, from about 20 to about 30, or from about 25 to about 30 nucleotides in length. Additionally, or alternatively, the 5'-tail regions of the 5'-tailed primers can have a higher G-C content as compared to the hybridization region. For example, the 5'-tail region can have, or have at least, 1, 2, 3, 4, 5, 6, 7, 8, 9, 10, 11, 12, 13, 14, or 15 more G or C nucleotides as compared to the hybridization region. As another example, the 5'-tail region can have from about 1 to about 3, from about 1 to about 5, from about 1 to about 10, from about 2 to about 3, from about 2 to about or from about 2 to about 10 more G or C nucleotides as compared to the hybridization region.

ii. 5'-Tailed Primers for Split-Cycle Down Amplification

In some embodiments, the 5'-tailed forward and 5'-tailed reverse primers anneal to the target DNA template at a relatively high temperature as compared to the annealing of the flanking primers to the products of the first set of amplification cycles. Split-cycle amplification in which the annealing temperature of the 5'-tailed primers is higher than the annealing temperature of the flanking primers is referred to as split-cycle down amplification because the annealing temperature is lowered down in a second set of amplification cycles. In some cases, this difference in annealing temperatures can control whether extension of 5'-tailed primers or extension of flanking primers is predominantly performed in a reaction in a given cycle. For example, as explained in further detail below, 5'-tailed primer extension can be favored during a first set of amplification cycles having relatively high temperature annealing, and optionally primer extension, stages. Similarly, flanking primer extension can be favored during a second set of amplification cycles in which 5'-tailed primers are depleted and relatively low temperature annealing, and optionally primer extension stages, are employed.

Thus, the hybridization regions of the 5'-tailed primers can be longer than the hybridization regions of the flanking primers. In some embodiments, the hybridization regions of the 5'-tailed primers are at least about 10 nucleotides in length. In some cases, the hybridization regions of the 5'-tailed primers are, are about, are at least, or are at least about 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, or 45 nucleotides in length. In some cases, the hybridization regions of the 5'-tailed primers are from about 12 to about 45, from about 15 to about 40, from about 18 to about 35, from about 20 to about 30, from about 25 to about 30, from about 15 to about 30, from about 18 to about 25, from about 20 to about 25, or from about 15 to about 25 nucleotides in length.

Additionally, or alternatively, the hybridization regions of the 5'-tailed primers can have a higher G-C content, or be modified to exhibit an increased annealing temperature as compared to the flanking primers in the split-cycle reaction. In some cases, the hybridization regions of the 5'-tailed primers have an annealing temperature that is at least 1° C. higher than the highest hybridization temperature of the flanking primers in the split-cycle reaction. In some cases, the hybridization regions of the 5'-tailed primers have an annealing temperature that is, is about, is at least, or is at least about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, or ° C. higher than the highest hybridization temperature of the flanking primers in the split-cycle reaction. In some cases, the hybridization regions of the 5'-tailed primers have an annealing temperature that is from about 1° C. to about 45° C., from about 2° C. to about 35° C., from about 3° C. to about 30° C., from about 5° C. to about 20° C., from about 5° C. to about 15° C., or from about 5° C. to about 10° C. higher than the highest hybridization temperature of the flanking primers in the split-cycle reaction. In some cases, the hybridization regions of the 5'-tailed primers have an annealing temperature that is from about 1° C. to about 5° C., from about 2° C. to about 5° C., from about 3° C. to about 5° C., from about 1° C. to about 10° C., from about 2° C. to about 10° C., from about 3° C. to about 10° C., or from about 5° C. to about 10° C. higher than the highest hybridization temperature of the flanking primers in the split-cycle reaction. In some cases, the hybridization regions of the 5'-tailed primers have an annealing temperature that is from about 10° C. to about 25° C., from about 10° C. to about 30° C., from about 10° C. to about 35° C., from about 15° C. to about 25° C., from about 15° C. to about 30° C., from about 15° C. to about 35° C., or from about 20° C. to about 30° C. higher than the highest hybridization temperature of the flanking primers in the split-cycle reaction.

In some embodiments, the hybridization regions of the 5'-tailed primers have an annealing temperature of less than about 75° C. In some embodiments, the hybridization regions of the 5'-tailed primers have an annealing temperature of greater than about 50° C. (e.g., greater than about 50° C. and less than about 75° C.). In some embodiments, the hybridization regions of the 5'-tailed primers have an annealing temperature of from about 45° C. to about 75° C., from about 50° C. to about 70° C.; from about 55° C. to about 68° C.; from about 55° C. to about 65° C.; or from about 55° C. to about 60° C. In some embodiments, the hybridization regions of the 5'-tailed primers have an annealing temperature of, or of about, 50, 55, 60, 65, 68, 70, 72, or 75° C.

The 5'-tail regions of the 5'-tailed primers can be configured to provide a primer binding site for the corresponding flanking primer that has a lower annealing temperature than the annealing temperature of the 5-tailed primers. Additionally or alternatively, the 5'-tail regions can have a shorter length in nucleotides than the 3' hybridization regions. In some embodiments, the 5'-tail regions of the 5'-tailed primers are at least about 7 nucleotides in length. In some cases, the 5'-tail regions of the 5'-tailed primers are, are about, or are at least about 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, or 45 nucleotides in length. In some cases, the regions of the 5'-tailed primers are from about 7 to about 35, about 8 to about 30, about 9 to about 30, about 7 to about 30, about 8 to about 25, about 9 to about 20, about 7 to about 20, about 8 to about 18, about 9 to about 15 or about 8 to about 15, nucleotides in length. Additionally, or alternatively, the 5'-tail regions of the 5'-tailed primers can have a lower G-C content as compared to the hybridization region. For example, the 5'-tail region can have, or have at least, 1, 2, 3, 4, 5, 6, 7, 8, 9, 10, 11, 12, 13, 14, or 15 fewer G or C nucleotides as compared to the hybridization region.

In some embodiments, the flanking primers have an annealing temperature of at least about 45° C. In some embodiments, the flanking primers have an annealing temperature of from about 45° C. to about 80° C., from about 45° C. to about 75° C.; from about 45° C. to about 65° C.; from about 45° C. to about 60° C.; or from about 45° C. to about 55° C. In some embodiments, the flanking primers have an annealing temperature of, or of about, 45, 50, 55, 60, 65, 70, or 75° C.

Flanking primers are typically the same length as the 5'-tail regions of the corresponding 5'-tailed primers. However, flanking primers can be shorter than the 5'-tail region or can contain additional nucleotides, detectable labels, etc. In some embodiments, the flanking primers are at least about 8 nucleotides in length. In some cases, the flanking primers are 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, or 45 nucleotides in length. In some cases, the flanking primers are from about 7 to about 15, about 8 to about 15, about 9 to about 25, about 10 to about 45, about 11 to about 40, about 12 to about 35, about 10 to about 30, about 11 to about about 12 to about 30, or about 15 to about 30, nucleotides in length.

Flanking primers can be modified at one or more positions to increase or decrease annealing temperatures. Suitable modifications to increase annealing temperature include, but are not limited to, one or more of the modifications selected from 2' fluoro nucleosides, LNAs (locked nucleic acids), ZNAs (zip nucleic acids), and PNAs (Peptide Nucleic Acids). Suitable modifications to decrease annealing temperature include, but are not limited to, base and backbone modifications. Base modifications that alter the Watson-Crick interaction between opposite bases include inosine, xanthosine, oxo-guanine, etc. Backbone modifications such as acyclic nucleoside analogues lower the melting temperature without affecting the Watson-Crick interaction (Nielsen, P., Dreiøe, L. H. & Wengel, J. Synthesis and evaluation of oligodeoxynucleotides containing acyclic)). Another backbone modification known to decrease annealing temperature can be considered an abasic site (Hianik, T. et al. DNA-duplexes containing abasic sites: correlation between thermostability and acoustic wave properties. Analyst 131, 1161-1166 (2006)) or linker that completely lacks a base to form a pair with the opposite strand.

In some embodiments, one or more flanking primers can include a detectable label (e.g., fluorescent label). In some cases, split-cycle reaction mixtures in which one or more flanking primers include a detectable fluorescent label also include a short oligonucleotide that includes a quencher and is reverse complementary to the fluorescently labeled flanking primer. In some cases, such reaction mixtures include a thermostable polymerase with strand-displacing activity. In some cases, amplification in the presence of a fluorescently labeled flanking primer, quencher, and strand-displacing polymerase is performed with an Amplicon Mediated Probe assay (AMP assay). Such assays are described further in US 2015/0,148,250, herein incorporated by reference in the entirety for all purposes. In some embodiments, flanking primers having a detectable label conjugated thereto are useful for split-cycle down amplification reactions, in which the annealing temperature is lowered in the second set of amplification cycles. In some embodiments, flanking primers having a detectable label conjugated thereto are useful for split-cycle up amplification reactions in which the annealing temperature is raised in the second set of amplification cycles.

In some embodiments, 5'-tailed primers are provided in the split-cycle amplification reaction at a lower concentration as compared to flanking primers. Lower concentration 5'-tailed primers can be useful, e.g., to rapidly deplete 5'-tailed primers during early rounds of amplification and ensure that later amplification cycles are predominantly performed by hybridization and extension of flanking primers. Thus, in some embodiments, the 5'-tailed primers are at a concentration that is less than about 50% (i.e., less than about ½) of the concentration of the flanking primers. As used herein, the term 50%, half, one-half, or ½, in reference to the concentration of a first pair off primers (e.g., 5'-tailed primers) to a second pair of primers (e.g., flanking primers) refers to a numerical concentration value for the first pair of primers that is one-half the concentration value for the second pair of primers. Thus, for the purposes of illustration only, for a first pair of primers at 1 µM in a reaction mixture and at ½ the concentration of a second pair of primers in the reaction mixture, the second pair of primers will be at 2 µM. One of skill in the art will appreciate that an alternative percentage or range of percentage of reduced or increased concentration can be similarly calculated and understood by those of ordinary skill in the art. Generally, the individual primers of a primer pair are at, or at about, equimolar concentration with respect to each other.

In some embodiments, the 5'-tailed primers are at a concentration that is from at least about 0.0001% to at least about ½ (i.e., 50%) of the concentration of the flanking primers. In some embodiments, the 5'-tailed primers are at a concentration that is from at least about 0.001% to at least about ½ (i.e., 50%) of the concentration of the flanking primers. In some embodiments, the 5'-tailed primers are at a concentration that is from at least about 0.01% to no more than about ½ (i.e., 50%) of the concentration of the flanking primers. In some embodiments, the 5'-tailed primers are at a concentration that is from at least about 0.1% to no more than about ½ (i.e., 50%) of the concentration of the flanking primers. In some embodiments, the 5'-tailed primers are at a concentration that is from at least about 1% to no more than about ½ (i.e., 50%) of the concentration of the flanking primers. In some embodiments, the 5'-tailed primers are at a concentration that is from at least about 5% to no more than about ½ (i.e., 50%) of the concentration of the flanking primers. In some embodiments, the 5'-tailed primers are at a concentration that is from at least about 10% to no more than about ½ (i.e., 50%) of the concentration of the flanking primers. In some embodiments, the 5'-tailed primers are at a concentration that is from at least about 15% to no more than about ½ (i.e., 50%) of the concentration of the flanking primers. In some embodiments, the 5'-tailed primers are at a concentration that is from at least about 20% to no more than about ½ (i.e., 50%) of the concentration of the flanking primers. In some cases, the primers are at a concentration that is, or is about, the concentration of the flanking primers.

In some cases, relative primer concentrations, e.g., in combination with relative annealing temperatures, of the 5'-tailed primers as compared to the corresponding flanking primers can provide control of whether extension of 5'-tailed primers or extension of flanking primers is predominantly performed in a reaction in a given cycle. For example, low-temperature annealing 5'-tailed primers can be provided in a split-cycle amplification reaction at a higher concentration than high-temperature annealing flanking primers. Thus, amplification cycles having a low temperature annealing stage can predominantly extend hybridized 5'-tailed primers even though flanking primers can anneal at such temperatures, while high temperature annealing cycles can predominantly extend hybridized flanking primers because annealing of 5'-tailed primers at the higher annealing temperature is disfavored.

Thus, in some embodiments, the 5'-tailed primers are at a concentration that is from at least about 2-fold to at least about 10,000-fold higher than the concentration of the flanking primers. In some embodiments, the 5'-tailed primers are at a concentration that is from at least about 2-fold and no more than about 10,000-fold higher than the concentration of the flanking primers. In some cases, the 5'-tailed primers are at a concentration that is, or is about, 5-fold; 15-fold; 20-fold, 30-fold, 50-fold, 75-fold; 100-fold, 250-fold; 500-fold; or 1,000-fold higher than the concentration of the flanking primers. In some cases, the 5'-tailed primers are at a concentration that is from at least about 2-fold to no more than about 1,000-fold, from at least about 2-fold to no more than about 500-fold, from at least about 2-fold to no more than about 100-fold, from at least about 2-fold to no more than about 50-fold, from at least about 2-fold to no more than about 10-fold, or from at least about 2-fold to no more than 5-fold higher than the concentration of the flanking primers.

Similarly, high-temperature annealing 5'-tailed primers can be provided in a split-cycle amplification reaction at a lower concentration than low-temperature annealing flanking primers. Thus, initial amplification cycles having a high temperature annealing stage can predominantly extend and deplete hybridized 5'-tailed primers, while subsequent low temperature annealing cycles can predominantly extend hybridized flanking primers because the tailed primers are depleted.

Thus, in some embodiments, the flanking primers are at a concentration that is from at least about 2-fold to at least about 10,000-fold higher than the concentration of the 5'-tailed primers. In some embodiments, the flanking primers are at a concentration that is from at least about 2-fold and no more than about 10,000-fold higher than the concentration of the 5'-tailed primers. In some cases, the flanking primers are at a concentration that is, or is about, 5-fold; 10-fold; 15-fold; 20-fold, 30-fold, 50-fold, 75-fold; 100-fold, 250-fold; 500-fold; or 1,000-fold higher than the concentration of the 5'-tailed primers.

The total primer concentration of the split-cycle amplification reaction can be from about 1 nM to about 1 µM, from about 5 nM to about 900 nM, from about 10 nM to about 750 nM, from about 15 nM to about 600 nM, from about 20 nM to about 500 nM, from about 25 nM to about 400 nM, from about 50 nM to about 300 nM, from about 75 nM to about 250 nM, or from about 100 nM to about 200 nM. In some cases, the total primer concentration in the split-cycle amplification reaction is, or is about, 25, 30, 35, 40, 45, 50, 55, 60, 65, 70, 75, 80, 90, 100, 110, 120, 130, 140, 150, 160, 170, 180, 190, 200, 225, 250, 275, 300, 350, 400, or 500 nM.

Split-cycle amplification compositions and methods, such as those described herein, can increase the sensitivity of a nucleic acid amplification assay by, e.g., lowering variations due to mis-priming or polymerase-mediated nucleotide mis-incorporation errors. For example, in an amplification reaction in which the 3' hybridization regions of the 5'-tailed primers hybridize to a target template sequence that is highly similar to a non-target sequence, early amplification cycles, in which 5'-tailed primer extension predominates, can exhibit significant mis-priming of primer to non-target templates. Similarly, during polymerase-mediated nucleotide mis-incorporation hybridization of a 5'-tailed primer to a target site can produce a non-target mutant primer-extension product that is not, or not efficiently, amplified by additional rounds of 5'-tailed primer-mediated amplification. In contrast later amplification cycles, in which extension of flanking primers predominates, can be highly resistant to mis-priming and/or mis-incorporation errors because the flanking primer binding site can be significantly different from any other sequence in the sample.

By limiting the effect of mis-priming and/or mis-incorporation to a small number of early amplification cycles, the assay can exhibit increased sensitivity. Such errors due to mis-priming or polymerase nucleotide mis-incorporation be substantial during, e.g., variant analysis, such as where the difference between target and non-target is a single nucleotide (e.g., SNP analysis). These mis-priming or polymerase nucleotide mis-incorporation errors can also substantial in a multi-channel assays where two or more target templates differ by a small number of nucleotides. For example, in an assay where mutant and target templates are separately detected, it can be beneficial to limit the effects of mis-priming and/or mis-incorporation to a small number of early amplification cycles.

Accordingly, in some embodiments, the split-cycle reaction mixtures described herein contain two sets of 5'-tailed forward and reverse primer pairs and two sets of forward and reverse flanking primer pairs. For example, the split-cycle reaction mixtures described herein can include a wild-type specific 5'-tailed forward and reverse primer pair that hybridizes to a target DNA template containing wild-type target sequence and a mutation-specific 5'-tailed forward and reverse primer pair that hybridizes to a target DNA template containing a mutant target sequence. Such reaction mixtures further contain two corresponding sets of flanking forward and reverse primer pairs.

In some cases, the difference between the wild-type target sequence and the mutant target sequence is 1, 2, 3, 4, 5, 6, 7, 8, 9, or 10 nucleotides. Accordingly, in some cases, the hybridization regions of the wild-type and mutation-specific 5'-tailed forward primers differ by 1, 2, 3, 4, 5, 6, 7, 8, 9, or 10 nucleotides. Similarly, in some cases, the hybridization regions of the wild-type and mutation-specific 5'-tailed reverse primers differ by 1, 2, 3, 4, 5, 6, 7, 8, 9, or nucleotides. In some cases, wild-type specific and mutation-specific 5'-tailed forward primers and wild-type specific and mutation-specific 5'-tailed reverse primers independently differ by, or by about, 1, 2, 3, 4, 5, 6, 7, 8, 9, or 10 nucleotides. In contrast, the 5'-tail regions and flanking primers are generally selected to be substantially different from each other, such that flanking primers do not cross-hybridize to non-target tail regions under amplification reaction conditions.

In some cases, the mutation-specific 5'-tailed primers contain a discriminatory nucleotide within the first 5 nucleotides of the 3' hybridization region, counting from the 3' end, that discriminate between mutant and wild-type target sequence. For example, the mutation-specific 5'-tailed primers can contain a discriminatory nucleotide that is the 3'-most nucleotide, the second-most 3' nucleotide, the third-most 3' nucleotide, the fourth-most 3' nucleotide, or the fifth-most 3' nucleotide. In some cases, the mutation-specific 5'-tailed primers contain multiple discriminatory nucleotides. In some cases, the discriminatory nucleotides are adjacent. In some cases, the forward and reverse 5'-tailed primers each contain a discriminatory nucleotide.

In some embodiments, a reaction mixture for performing a split-cycle nucleic acid amplification assay includes: a thermostable polymerase; any one or more of the foregoing target-specific forward and reverse 5'-tailed primer pairs; and any one or more of the foregoing target-specific forward and reverse flanking primer pairs. In some cases, the target-specific forward and reverse 5'-tailed primer pair specifically hybridizes to and amplifies a wild-type nucleic acid target sequence. In some cases, the target-specific forward and reverse 5'-tailed primer pair specifically hybridizes to and amplifies a mutant nucleic acid target sequence. In some cases, the reaction mixture contains both a mutation-specific forward and reverse 5'-tailed primer pair and a wild-type specific forward and reverse 5'-tailed primer pair. In some cases, the reaction mixture contains one or more additional target-specific forward and reverse 5'-tailed primer pairs that specifically hybridize to and amplify one or more additional target nucleic acids. Reaction mixtures containing multiple forward and reverse 5'-tailed primer pairs can contain a corresponding number of forward and reverse flanking primer pairs where each flanking primer pair specifically amplifies amplicons generated by the corresponding 5'-tailed primer pair.

In some embodiments, a reaction mixture for performing a split-cycle nucleic acid amplification assay includes: i) a target-specific forward 5'-tailed primer and target-specific reverse 5'-tailed primer (i.e., a target-specific 5'-tailed primer pair), where the target-specific 5'-tailed primer pair hybridizes to and specifically amplifies target DNA template molecules from a nucleic acid sample that contain the target sequence, if present, and where the primers of the target specific 5'-tailed primer pair include: a) a 3' hybridization region of at least 10 nucleotides in length and less than 30 nucleotides in length that specifically hybridizes to the mutant target sequence; and b) a target-specific 5' tail region of at least 10 nucleotides in length and no more than 30 nucleotides in length that does not hybridize to any nucleic acid fragments in the nucleic acid sample. In some cases, the reaction mixture further contains: ii) a pair of forward and reverse target-specific flanking primers, wherein the target-specific flanking primers hybridize to and specifically amplify amplicons containing the 5' tail regions of the target-specific 5'-tailed primer pair if present.

Split-cycle reaction mixtures can further contain amplification reagents as known in the art. Such amplification reagents include, but are not limited to, nucleotide triphosphates, divalent cation, buffer, salt, stabilizers, and other additives (e.g., betaine, DMSO, etc.). In some cases, the split-cycle reaction mixtures contain an intercalating dye, e.g., EvaGreen. Such intercalating dyes can be useful for detecting amplification in a reaction where single-channel detection is desired. For example, in a split-cycle amplification containing a single set of 5'-tailed forward and reverse primers and a single set of corresponding flanking primers, an intercalating dye can discriminate between a reaction mixture containing amplicons, indicating the presence of target DNA template, and a reaction mixture that does not contain a substantial number of amplicons, indicating the absence of sufficient target DNA template.

Alternatively, sequence specific probes can be present in the split-cycle reaction mixture. Sequence specific probes can be useful for single-channel detection as described above. Sequence specific probes can also be useful for multi-channel detection. For example, in an split-cycle assay in which two or more different amplicons are generated using two or more different sets of 5'-tailed primer pairs and corresponding flanking primer pairs, sequence-specific probes can discriminate between the two or more different amplicons. Exemplary sequence-specific probes include, but are not limited to hydrolysis probes (e.g., TAQMAN), and Molecular Beacons. Alternatively, as described above, the flanking primers can be detectably labeled sequence specific probes. In some embodiments, reaction mixtures including detectably labeled flanking primers also include a sink oligonucleotide that quenches the detectable label when hybridized to the flanking primer. Disruption of the flanking primer:sink oligonucleotide hybrid by, e.g., polymerase mediated hydrolysis, results in a detectable signal indicating the presence of the target nucleic acid.

b. Partitioned Split-Cycle Compositions

Split-cycle amplification can be performed on a partitioned nucleic acid sample in a plurality of mixture partitions. In some embodiments, accurate quantitation of target template molecules in the sample requires that the plurality of mixture partitions produced by partitioning of the nucleic acid sample is not saturated by the number of target template molecules in the sample. As such, described herein are split-cycle compositions containing a plurality of mixture partitions, where the individual mixture partitions are generated by partitioning the nucleic acid sample, and the plurality contains at least about 1 mixture partition that does not contain a target template molecule (e.g., wild-type or mutant).

In some embodiments, the plurality contains about, or at least about, 2-10 or 3-10 mixture partitions that do not contain a template molecule (e.g., wild-type or mutant). In some embodiments, the plurality contains about 10; 20; 30; 40; 50; 60; 100; 1,000; 2,000; 3,000; 4,000; 5,000; 10,000; 15,000, or more mixture partitions that do not contain a template molecule. In some embodiments about, or at least about, 0.001%, 0.005%, 0.01%, 0.05%, 0.1%, 1%, 2%, 3%, 4%, 6%, 7%, 8%, 9%, 10%, 15%, 20%, 25%, 30%, 35%, 40%, 50%, 55%, 60%, 65%, 70%, 75%, 80%, 85%, or 90% of the mixture partitions do not contain a template molecule. In some embodiments, from about 0.001% to about 50% of the mixture partitions do not contain a template molecule. In some embodiments, from about 0.005% to about 25% of the mixture partitions do not contain a template molecule. In some embodiments, from about 0.1% to about 15% of the mixture partitions do not contain a template molecule. In some embodiments, from about 1% to about 10% of the mixture partitions do not contain a template molecule. In some embodiments, from about 10% to about 50% of the mixture partitions do not contain a template molecule.

In some embodiments, the target template molecules are present in the plurality of mixture partitions at a concentration of at least about 0.000025 copies per partition. In some embodiments, the target template molecules are present in the plurality of mixture partitions at a concentration of from about 0.000025 to about 50 copies per partition, from about 0.0001 to about 50 copies per partition, from about 0.0005 to about 50 copies per partition, from about to 40 copies per partition, from about 0.005 to about 30 copies per partition, from about to about 20 copies per partition, or from about 0.00005 to about 20 copies per partition. In some embodiments, the target template molecules are present in the plurality of mixture partitions at a concentration of from about 0.025 to about 30 copies per partition, from about 0.05 to about 30 copies per partition, from about 0.01 to about 30 copies per partition, from about 0.25 to about 30 copies per partition, from about 0.025 to about 10 copies per partition, from about 0.05 to about 10 copies per partition, from about 0.01 to about 10, or from about 0.25 to about 10 copies per partition. In some cases, the target DNA template in the mixture is at an average concentration of, or of about, 0.00025, 0.0005, 0.00075, 0.001, 0.0025, 0.005, 0.0075, 0.01, 0.025, 0.05, 0.075, 0.1, 0.25, 0.5, 0.75, 1, 1.25, 1.5, 1.75, 2, 2.5, 3, 3.5, 4, 4.5, 5, 5.5, 6, 6.5, 7, 7.5, 8, 8.5, 9, 9.5, 10, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 copies per partition.

In some embodiments, the plurality of mixture partitions contains one or more wild-type target template molecules. In some embodiments, the plurality of mixture partitions contains target template molecules having a mutant target sequence. In some embodiments, the plurality of mixture partitions contains at least one target template molecule having a mutant target sequence and a plurality of wild-type target template molecules.

In some embodiments, at least one of the plurality of mixture partitions contains both a wild-type target template molecule and a mutant target template molecule. In some embodiments, about 0.0001%, or at least 0.0001%, of the plurality of mixture partitions contains a wild-type target template molecule and a mutant target template molecule. In some embodiments, about 0.001%, or at least 0.001%, of the plurality of mixture partitions contains a wild-type target template molecule and a mutant target template molecule. In some embodiments, about 0.01%, or at least 0.01%, of the plurality of mixture partitions contains a wild-type target template molecule and a mutant target template molecule. In some embodiments, about 0.1%, or at least 0.1%, of the plurality of mixture partitions contains a wild-type target template molecule and a mutant target template molecule. In some embodiments, about 1%, or at least 1%, of the plurality of mixture partitions contains a wild-type target template molecule and a mutant target template molecule. In some embodiments, about, or at least about, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45% of the plurality of mixture partitions contains a wild-type target template molecule and a mutant target template molecule.

In some embodiments, the number of mixture partitions in the plurality of mixture partitions is at least about 100. In some embodiments, the number of mixture partitions in the plurality of mixture partitions is from about 100 to about 10,000,000; from about 500 to about from about 500 to about 200,000; from about 500 to about 100,000; from about 500 to about 75,000; from about 1,000 to about 50,000; or from about 5,000 to about 20,000. In some embodiments, the number of mixture partitions in the plurality of mixture partitions is, or is about, 500; 750; 1,000; 2,000; 3,000; 4,000; 5,000; 7,500; 5,000; 7,500; 10,000; 15,000; 30,000; 40,000; 50,000; 75,000; 100,000; 150,000; 200,000; 500,000; 1,000,000; or 10,000,000.

c. Tagged Amplicon Primer Extension (TAPE) Compositions

Described herein are compositions for performing tagged amplicon primer extension (TAPE) reactions. In one aspect, the composition is a set of TAPE primers. TAPE primers are pairs of PCR nucleic acid amplification primers that contain 5' tails, where the 5' tails of the individual primers of the pair are reverse complements of each other. In some cases, the TAPE primers are also split-cycle 5'-tailed primers.

TAPE forward and reverse primers can contain a 3' hybridization region that is configured to specifically hybridize to a target sequence of a target DNA template molecule and generate a first primer extension product in a nucleic acid amplification reaction. In some cases, the 3' hybridization region is at least about 8 nucleotides in length. In some cases, the hybridization regions of the TAPE primers are 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, or 45 nucleotides in length. In some cases, the hybridization regions of the TAPE primers are from about 8 to about 45, about 9 to about 40, about 8 to about 35, about 8 to about 30, about 9 to about 30, about 10 to about 30, about 11 to about 25, about 12 to about 25, or about 15 to about nucleotides in length.

TAPE forward and reverse primers can contain a 5' tail region that is not complementary to the target sequence of the target DNA template molecule. In some cases, the tail region is at least about 8 nucleotides in length. In some cases, the 5' tail regions of the TAPE primers are 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, or 45 nucleotides in length. In some cases, the 5' tail regions of the TAPE primers are from about 8 to about 45, about 9 to about 40, about 8 to about 35, about 8 to about 30, about 9 to about 30, about 10 to about 30, about 11 to about 25, about 12 to about 25, or about 15 to about 25, nucleotides in length.

In some cases, the TAPE primers contain a discriminatory nucleotide within the first 5 nucleotides of the 3' hybridization region, counting from the 3' end, that discriminate between a mutant and wild-type target sequence. For example, the discriminatory nucleotide can be the 3'-most nucleotide, the second-most 3' nucleotide, the third-most 3' nucleotide, the fourth-most 3' nucleotide, or the fifth-most 3' nucleotide. In some cases, the TAPE primers contain multiple discriminatory nucleotides. In some cases, the multiple discriminatory nucleotides are adjacent. In some cases, the forward and reverse TAPE primers each contain a discriminatory nucleotide.

In some embodiments, the 5' tail regions of the forward and/or reverse TAPE primers contain a restriction endonuclease cleavage site. The restriction endonuclease cleavage site can be useful to cleave amplicon concatemers generated in the TAPE reaction. In some cases, both forward and reverse TAPE primers contain a restriction endonuclease cleavage site. In some cases, both forward and reverse TAPE primers contain the same restriction endonuclease cleavage site. In some cases, the forward and reverse TAPE primers contain different restriction endonuclease cleavage sites.

In some cases, the TAPE reaction mixture further contains a pair of forward and reverse flanking primers that specifically hybridizes to and amplifies amplicons containing the 5' tail regions of the TAPE primers.

In some cases, the TAPE reaction contains a first forward and reverse TAPE primer pair that specifically hybridizes to and amplifies a first target sequence and a second forward and reverse TAPE primer pair that specifically hybridizes to and amplifies a second target sequence. In some cases, the first and second target sequences are a wild-type and corresponding mutant target sequence respectively. Accordingly, the first TAPE primer pair can be a wild-type specific TAPE primer pair having a 3' hybridization region that specifically hybridizes to and amplifies target template molecules having the wild-type target sequence. In some cases, the forward and/or reverse primers of the first TAPE primer pair can contain a discriminatory nucleotide in the 3' hybridization region that is complementary to the wild-type target DNA template molecule but not the mutant target DNA template molecule.

Similarly, the second TAPE primer pair can be a mutation-specific TAPE primer pair having a 3' hybridization region that specifically hybridizes to and amplifies target template molecules having a mutant target sequence. In some cases, the forward and/or reverse primers of the second TAPE primer pair can contain a discriminatory nucleotide in the 3' hybridization region that is complementary to the mutant target DNA template molecule but not the wild-type target DNA template molecule.

In some cases, the 5' tails of the first set of forward and reverse TAPE primers are different from the 5' tails of the second set of forward and reverse TAPE primers. In some cases, the TAPE reaction mixture further contains a first pair of forward and reverse flanking primers that specifically hybridizes to and amplifies amplicons containing the 5' tail regions of the first set of TAPE primers. In some cases, the TAPE reaction mixture further contains a second pair of forward and reverse flanking primers that specifically hybridizes to and amplifies amplicons containing the 5' tail regions of the second set of TAPE primers.

TAPE reactions can contain any one or more of the foregoing nucleic acid amplification reaction compositions or mixtures described herein, including but not limited to, primers, probes, buffers, salts, polymerases, or the like, and combinations thereof. TAPE reactions can be performed in a plurality of mixture partitions. As such, TAPE reaction compositions can include, but are not limited to, any one or more of the foregoing partitioned split-cycle compositions described herein, including but not limited to, those containing mutant and wild-type targets, those containing 1 or more partitions that do not contain a target template molecule, those containing 1 or more partitions that do contain a target template molecule, or those containing 1 or more partitions that contain both a wild-type and target template molecule, and combinations thereof.

III. Methods a. Split-Cycle

Described herein are methods for quantitating an absolute number or frequency of wild-type and mutant target nucleic acid fragments in a nucleic acid sample. In some embodiments, the method includes forming a plurality of mixture partitions containing a fraction of the nucleic acid sample, one or more of the foregoing pairs of 5'-tailed primers, one or more of the foregoing pairs of flanking primers and a thermostable polymerase. In some cases, the mixture partitions are emulsion droplets.

The method can include an incubation under thermal cycling conditions suitable for amplification of target DNA template molecules, if present, by a polymerase chain reaction. In some cases, the thermal cycling conditions include a first set of temperature cycles (e.g., a first set of denaturing, annealing, and extending) and a second set of temperature cycles (e.g., a first set of denaturing, annealing, and extending), where the annealing step of the second set of temperature cycles is at least 1° C. higher than the annealing step of the first set of temperature cycles. In some cases, the annealing step of the second set of temperature cycles is 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, or 45° C. higher than the annealing step of the first set of temperature cycles. In some cases, the annealing step of the second set of temperature cycles is from about 1 to about 5° C., from about 1 to about 10° C., or from about 1 to about 15° C. higher than the annealing step of the first set of temperature cycles. In some cases, the annealing step of the second set of temperature cycles is from about 2 to about 5° C., from about 2 to about ° C., or from about 2 to about 15° C. higher than the annealing step of the first set of temperature cycles. In some cases, the annealing step of the second set of temperature cycles is from about 5 to about 10° C., from about 5 to about 15° C., or from about 5 to about 20° C. higher than the annealing step of the first set of temperature cycles.

In some cases, the thermal cycling conditions include a first set of temperature cycles (e.g., a first set of denaturing, annealing, and extending) and a second set of temperature cycles (e.g., a first set of denaturing, annealing, and extending), where the annealing step of the second set of temperature cycles is at least 1° C. lower than the annealing step of the first set of temperature cycles. In some cases, the annealing step of the second set of temperature cycles is 1, 2, 3, 4, 5, 6, 7, 8, 9, 10, 11, 12, 13, 14, 15, 16, 17, 18, 19, 20, 21, 22, 23, 24, 25, 26, 27, 28, 29, 31, 32, 33, 34, 35, 36, 37, 38, 39, 40, 41, 42, 43, 44, or 45° C. lower than the annealing step of the first set of temperature cycles. In some cases, the annealing step of the second set of temperature cycles is from about 1 to about 5° C., from about 1 to about 10° C., or from about 1 to about 15° C. lower than the annealing step of the first set of temperature cycles. In some cases, the annealing step of the second set of temperature cycles is from about 2 to about 5° C., from about 2 to about 10° C., or from about 2 to about 15° C. lower than the annealing step of the first set of temperature cycles. In some cases, the annealing step of the second set of temperature cycles is from about 5 to about 10° C., from about 5 to about 15° C., or from about 5 to about 20° C. lower than the annealing step of the first set of temperature cycles.

In some embodiments, the method includes a step of detecting the presence or absence of amplified target DNA template in the mixture partitions. The detecting can thereby determine: i) the number of single-positive wild-type mixture partitions containing amplified target DNA template having a wild-type target sequence; ii) the number of single-positive mutant mixture partitions containing amplified target DNA template having a mutant target sequence; and iii) the number of double-positive mixture partitions containing both wild-type and mutant amplified target DNA. In some cases, the numbers of single-positive and double-positive partitions are used to determine the absolute quantity or frequency of wild-type and mutant target nucleic acid fragments in the nucleic acid sample. In some cases, the number of negative partitions, or the total number of all partitions is also used to calculate the absolute number or frequency of wild-type and mutant target nucleic acid fragments in the nucleic acid sample. The detecting can be detecting fluorescence of an intercalating dye, detecting fluorescence of a fluorophore conjugated to a flanking primer (e.g., with an AMP assay, see US 2015/0,148,250, herein incorporated by reference in the entirety for all purposes.), or detecting a fluorescence signal generated by polymerase-mediated hydrolysis of a nucleic acid hydrolysis probe.

In some embodiments, the first set of thermal cycling conditions is, or includes at least, a single denaturing, annealing, and extension step. In some cases, the first set of thermal cycling conditions includes from about 1 about 20, from about 2 to about 15, or from about 2 to about 5 cycles of denaturing, annealing, and extension. In some embodiments, the second set of thermal cycling conditions is, or includes at least, 5 cycles of denaturing, annealing, and extension. In some cases, the second set of thermal cycling conditions includes from about 5 about 60, from about 10 to about 50, from about 15 to about 30, or from about 15 to about 25 cycles of denaturing, annealing, and extension. In some cases, the flanking primers in the reaction mixture have an annealing temperature at, or near (e.g., within about 1, 2, 3, 4, 5, 6, 7, 8, 9, or 10° C.), an optimal extension temperature of the polymerase and the annealing and extension in the second set of temperature cycles are performed simultaneously. In some cases, the 5'-tailed primers in the reaction mixture have an annealing temperature at, or near (e.g., within about 1, 2, 3, 4, 5, 6, 7, 8, 9, or 10° C.), an optimal extension temperature of the polymerase and the annealing and extension in the first set of temperature cycles are performed simultaneously.

b. Tagged Amplicon Primer Extension (TAPE)

Described herein are methods for performing a TAPE reaction. In one aspect, the method includes forming or providing any one of the foregoing reaction mixtures or plurality of mixture partitions. The reaction mixtures or mixture partitions can include a thermostable polymerase and a pair of forward and reverse TAPE primers having 5' tails that are reverse complements of each other. In some embodiments, the reaction mixture or plurality of mixture partitions, or a portion thereof, contain a target DNA template molecule.

The reaction mixture or plurality of mixture partitions can be subject to conditions suitable to carry out hybridization (i.e., annealing) of the 3' hybridizing regions of forward TAPE primers to target template molecules, if present. Hybridized TAPE primers can be extended with the polymerase generating a first primer extension product. The first primer extension product can be hybridized to a reverse TAPE primer, which is then extended with the polymerase, thereby generating a second primer extension product. The 3' hybridizing regions of the forward TAPE primer can be hybridized to the second primer extension product and extended, thereby generating a third primer extension product. The second and third primer extension products together form a first double-stranded amplicon having 3' ends that are reverse complements of each other and 5' ends that are reverse complements of each other.

The method can further include denaturing the first double stranded amplicon and hybridizing the 3' ends of the first double stranded amplicon to each other. The hybridized 3' ends of the two strands of the first double stranded amplicon can be extended with the polymerase to form a second double stranded amplicon having 3' ends that are reverse complements of each other and 5' ends that are reverse complements of each other. The second double-stranded amplicon can be larger than the first. The method can further include: denaturing the second double stranded amplicon; hybridizing the 3' ends of the two strands of the second double stranded amplicon; and extended the hybridized 3' ends of the two strands of the second double-stranded amplicon with the polymerase to generate a third double-stranded amplicon having 3' ends that are reverse complements of each other and 5' ends that are reverse complements of each other. The third double-stranded amplicon can be larger than the second.

The denaturing, annealing, and extending of double stranded amplicons can be repeated a number of times, e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50, or more times. In some cases, the denaturing, annealing, and extending of double stranded amplicons is repeated from about 1 about 50, from about 2 to about 40, from about 5 to about 40, from about 10 to about 40, from about 15 to about 40, from about 20 to about 40, from about 5 to about 30, from about 10 to about 30, from about 15 to about 30, from about 20 to about 30, from about 5 to about 25, from about 10 to about 25, from about 15 to about 25, from about 5 to about 20, from about 10 to about 20, or from about 15 to about 20 cycles of denaturing, annealing, and extension. In some cases, the reverse complementary 3' ends of the double-stranded amplicons in the reaction mixture have an annealing temperature at, or near (e.g., within about 1, 2, 3, 4, 5, 6, 7, 8, 9, or 10° C.), an optimal extension temperature of the polymerase and the annealing and extension are performed simultaneously.

In some embodiments, the large size of the amplicons generated in late cycles of the TAPE reaction results in precipitation. The precipitation can be utilized to provide a readout of a presence or absence of a target template molecule in a reaction mixture or mixture partition. For example, precipitation can be detected by optical detection of turbidity at an ultraviolet or visible wavelength. Additional or alternative methods for detecting are described below. Alternatively, double-stranded amplicons can be cleaved to prevent or reduce precipitation or to reduce amplicons to a uniform size.

Accordingly, in some cases, a cleavage site is included in the 5' tails of the TAPE primers. The cleavage site can be a restriction endonuclease site, a uracil (e.g., cleavable by a uracil glycosylase enzyme), or a chemically cleavable linkage. Generally, the cleavage site is selected to minimize interference with template-directed DNA polymerase activity of the polymerase present in the reaction mixture or mixture partitions. In some cases, the cleavage site is a dialkoxysilane, 3'-(S)-phosphorothioate, 5'-(S)-phosphorothioate, 3'-(N)-phosphoramidate, 5'-(N)phosphoramidate linkage in the 5' tail region of one or both of the TAPE primers. In reaction mixtures or mixture partitions containing multiple pairs of TAPE primers, each TAPE primer, or TAPE primer pair can contain a cleavage site in the 5' tail region independently selected from a dialkoxysilane, 3'-(S)-phosphorothioate, 5'-(S)-phosphorothioate, 3'-(N)-phosphoramidate, or 5'-(N)phosphoramidate linkage, a restriction endonuclease cleavage site, and uracil. In some embodiments, some TAPE primers or primer pairs in a reaction mixture or mixture partition contain a cleavage site in a 5' tail and some do not.

TAPE primers containing cleavage sites in the 5' tail regions generate amplicons containing a cleavage site. In some embodiments, the TAPE reaction method includes a step of cleaving the cleavage sites of the amplicons. The cleavage can be performed in the mixture partitions or reaction mixture. In some cases, the cleavage is performed by an extended incubation (e.g., 5, 10, 15, 30, 45, 60, or 90 minutes) at an optimal cleavage enzyme temperature (e.g., 37° C.).

In some cases, the cleavage additionally or alternatively includes introducing into the reaction mixture or mixture partitions a cleavage reagent (e.g., enzyme or chemical). For example, in some cases, an electric field can be applied to an interface between a partition and a fluid to disrupt the interface and allow at least a portion of the fluid to enter the partition. As another example, one or more reagents can be directed to partitions in micro or nanoliter size wells via microfluidic techniques. Methods, compositions, and devices for injection of reagents into a partition can include, but are not limited to, those described in WO/2010/0151776.

TAPE amplification can be detected by detecting the presence of amplicons or digested amplicons using a variety means known in the art to determine the presence or absence of a target template in the reaction mixture or plurality of mixture partitions. In some cases, the TAPE reaction amplifies both wild-type and mutant target template molecules, and the detecting is performed with a differentially labeled wild-type specific probe and a mutant-specific probe. The probes can be nucleic acid hydrolysis probes, Molecular Beacons, Scorpion Probes, and the like.

In some cases, the TAPE reaction amplifies both wild-type and mutant target template molecules because a single pair of forward and reverse TAPE primers can hybridize to both wild-type and mutant target template molecules and be extended to generate amplicons. In some cases, the TAPE reaction amplifies both wild-type and mutant target template molecules using two different pairs of forward and reverse TAPE primers, one pair specifically amplifying wild-type target sequences and one pair specifically amplifying mutant target sequence. In some cases, the TAPE reaction specifically amplifies a target template molecule and detection can be performed with a sequence specific probe or a non-specific detection reagent such as an intercalating dye. In some cases, the TAPE reaction specifically amplifies a mutant target template molecule, e.g., in the presence of wild-type target template molecules if also present, and detection can be performed with a sequence specific probe or a non-specific detection reagent such as an intercalating dye. In some cases, the sequence specific probe detects a region of the amplicons that is the same in the wild-type and mutant target templates.

In some cases, the TAPE reaction further includes flanking primers as described above. In such TAPE reactions, the method can include split-cycle amplification methods and compositions as described above. For example TAPE amplification can be performed with a first set of amplification conditions for hybridizing and extending TAPE primers and strands of resulting double-stranded amplicons, and a second set of amplification conditions for hybridizing and extending flanking primers. In some cases, the primer annealing temperature of the second set of amplification conditions is higher than the annealing temperature of the first set of amplification conditions. In some cases, the primer annealing temperature of the second set of amplification conditions is lower than the annealing temperature of the first set of amplification conditions. In some cases, one or more flanking primers are detectably labeled. In some cases, detection of amplification in such TAPE reactions can be performed using a, Amplicon Mediated Probe assay (AMP assay). Such assays are described further in US 2015/0,148,250, herein incorporated by reference in the entirety for all purposes.

In some cases, a plurality of mixture partitions is provided or generated; and, a split-cycle reaction mixture, a TAPE amplification reaction, or a combination thereof is performed to separately detect wild-type and mutant target DNA template molecules in the plurality of mixture partitions, thereby detecting a number of mixture partitions that are positive for the presence of the mutant but not the wild-type target DNA template, a number of mixture partitions that are positive for a presence of the wild-type but not the mutant target DNA template, a number of mixture partitions that are positive for the presence of both the mutant and wild-type target DNA template, and a number of mixture partitions that are negative for the presence of mutant and wild-type target DNA template. The method can further include determining the frequency of the mutant sequence in the nucleic acid sample from the number of single-positive, double-positive, and negative mixture partitions.

c. General Partitioning Methods

Partitioning methods described in the section can be performed for TAPE reaction mixtures, split-cycle reaction mixtures, or reaction mixtures in which TAPE and split-cycle methods, or elements thereof, are performed.

Partitions can include any of a number of types of partitions, including solid partitions (e.g., wells, reaction chambers, or tubes) and fluid partitions (e.g., aqueous droplets within an oil phase). In some embodiments, the partitions are droplets. In some embodiments, the partitions are micro channels. Methods and compositions for partitioning a sample are described, for example, in published patent applications WO 2010/036352, US 2010/0173394, US 2011/0092373, and US 2011/0092376, the entire contents of each of which is incorporated by reference herein.

In some aspects, the number of partitions is chosen to ensure that a minority of, a substantial minority of, few, substantially no, or no partitions contain multiple target template molecules, contain both wild-type and mutant target template molecules, or both. In some aspect, the number of partitions is selected to ensure that a quantitative digital amplification assay is not saturated (i.e., there remains partitions that do not have any template molecules).

The number of partitions necessary to ensure adequate partitioning is dependent on a number of factors, including, but not limited to: (a) the number of template molecules in a nucleic acid sample; (b) the method of partitioning; and (e) the desired statistical significance. Partitioning of a nucleic acid sample containing template molecules such that few or no partitions contain multiple template molecules generally requires partitioning under dilute conditions that generate a large number of "empty" partitions that do not contain any template molecules. Thus, in some embodiments, it is preferred to partition under conditions that generate a significant number of partitions containing multiple target template molecules. In general, the number of partitions is at least about 500; 1000; 10000; or 20,000; 30,000; 50,000; or more. In some cases, only about 3-10, or at least about 3-10, partitions do not contain any target template molecules. In such cases, a significant number of partitions can contain multiple target template molecules. In some cases, the multiple target template molecules in an individual partition include both wild-type and mutant target template molecules. In some cases, the multiple target template molecules in an individual partition are all wild-type. In some cases, the multiple target template molecules in an individual partition are all mutant.

In some embodiments, reagents such as salts (e.g., divalent cation), buffers, enzymes (e.g., cleavage enzymes), substrates, nucleotides, primers, etc. are mixed together (e.g., with a sample) prior to partitioning, and then the sample is partitioned. In some cases, the reagents include a polymerase and the sample is partitioned shortly after mixing reagents together so that substantially all, or the majority, of polymerase activity occurs after partitioning. In other cases, the reagents are mixed at a temperature in which the polymerase proceeds slowly, or not at all, the sample is then partitioned, and the reaction temperature is adjusted to allow the polymerase reaction to proceed. For example, the reagents can be combined on ice, at less than 5° C., or at 0, 1, 2, 3, 4, 5, 6, 7, 8, 9, 10, 11, 12, 13, 14, 15, 16, 17, 18, 19, 20, 20-25, 25-30, or 30-35° C. or more. In general, one of skill in the art will know how to select a temperature at which one or more polymerase enzymes are not active. In some cases, a combination of temperature and time are utilized to avoid substantial polymerase activity prior to partitioning.

In some cases, reagents can be mixed using one or more hot start polymerases, such as a hot start DNA-dependent DNA polymerase. Thus, buffers, salts, nucleotides, labels, primers, enzymes, etc. can be mixed and then partitioned. Subsequently, the polymerization reaction, including multiple rounds of polymerization and/or amplification, can be initiated by heating the partition mixtures to activate the one or more hot-start polymerases.

Additionally, reagents can be mixed together without one or more reagents necessary to initiate an enzymatic reaction (e.g., polymerization and/or amplification). The mixture can then be partitioned into a set of first partition mixtures and then the one or more essential reagents can be provided by fusing the set of first partition mixtures with a set of second partition mixtures that provide the essential reagent. Alternatively, the essential reagent can be added to the first partition mixtures without forming second partition mixtures. For example, the essential reagent can diffuse into the set of first partition mixture water-in-oil droplets. As another example, the missing reagent can be directed to a set of micro channels which contain the set of first partition mixtures.

In some embodiments, reagents can be mixed together to form a reaction mixture, and partitioned. Subsequently, one or more additional reagents can be added to the partitions. For example, one or more reagents can be injected into the partitions. In some cases, an electric field can be applied to an interface between a partition and a fluid to disrupt the interface and allow at least a portion of the fluid to enter the partition. As another example, one or more reagents can be directed to partitions in micro or nanoliter size wells via microfluidic techniques. Methods, compositions, and devices for injection of reagents into a partition can include, but are not limited to, those described in WO/2010/0151776. Reagents that can be added by fusing partitions, injection, microfluidics or other means include but are not limited to amplification reagents, detection reagents, or combinations thereof. For example, DNA-dependent DNA polymerase (and, optionally, one or more primers) can be added into a partition to amplify a target template nucleic acid in the partition.

In some embodiments, a droplet comprises an emulsion composition, i.e., a mixture of immiscible fluids (e.g., water and oil). In some embodiments, a droplet is an aqueous droplet that is surrounded by an immiscible carrier fluid (e.g., oil). In some embodiments, a droplet is an oil droplet that is surrounded by an immiscible carrier fluid (e.g., an aqueous solution). In some embodiments, the droplets described herein are relatively stable and have minimal coalescence between two or more droplets. In some embodiments, less than 0.0001%, 0.0005%, 0.001%, 0.01%, 0.05%, 0.1%, 0.5%, 1%, 2%, 3%, 4%, 5%, 6%, 7%, 8%, 9%, or 10% of droplets generated from a sample coalesce with other droplets. The emulsions can also have limited flocculation, a process by which the dispersed phase comes out of suspension in flakes. In some embodiments, the droplet is formed by flowing an oil phase through an aqueous sample comprising one or more of the compositions described herein.

The oil phase can comprise a fluorinated base oil which can additionally be stabilized by combination with a fluorinated surfactant such as a perfluorinated polyether. In some embodiments, the base oil comprises one or more of a HFE 7500, FC-40, FC-43, FC-70, or another common fluorinated oil. In some embodiments, the oil phase comprises an anionic fluorosurfactant. In some embodiments, the anionic fluorosurfactant is Ammonium Krytox (Krytox-AS), the ammonium salt of Krytox FSH, or a morpholino derivative of Krytox FSH. Krytox-AS can be present at a concentration of about 0.1%, 0.2%, 0.3%, 0.4%, 0.5%, 0.6%, 0.8%, 0.9%, 1.0%, 2.0%, 3.0%, or 4.0% (w/w). In some embodiments, the concentration of Krytox-AS is about 1.8%. In some embodiments, the concentration of Krytox-AS is about 1.62%. Morpholino derivative of Krytox FSH can be present at a concentration of about 0.1%, 0.3%, 0.4%, 0.5%, 0.6%, 0.7%, 0.8%, 0.9%, 1.0%, 2.0%, 3.0%, or 4.0% (w/w). In some embodiments, the concentration of morpholino derivative of Krytox FSH is about 1.8%. In some embodiments, the concentration of morpholino derivative of Krytox FSH is about 1.62%.

In some embodiments, the oil phase further comprises an additive for tuning the oil properties, such as vapor pressure, viscosity, or surface tension. Non-limiting examples include perfluorooctanol and 1H,1H,2H,2H-Perfluorodecanol. In some embodiments, 1H,1H,2H,2H-Perfluorodecanol is added to a concentration of about 0.05%, 0.06%, 0.07%, 0.08%, 0.09%, 0.2%, 0.3%, 0.4%, 0.5%, 0.6%, 0.7%, 0.8%, 0.9%, 1.0%, 1.25%, 1.50%, 1.75%, 2.0%, 2.25%, 2.5%, 2.75%, or 3.0% (w/w). In some embodiments, 1H,1H,2H,2H-Perfluorodecanol is added to a concentration of about 0.18% (w/w).

In some embodiments, the emulsion is formulated to produce highly monodisperse droplets having a liquid-like interfacial film that can be converted by heating into microcapsules having a solid-like interfacial film; such microcapsules can behave as bioreactors able to retain their contents through an incubation period. The conversion to microcapsule form can occur upon heating. For example, such conversion can occur at a temperature of greater than about 50°, 60°, 70°, 80°, 90°, or 95° C. During the heating process, a fluid or mineral oil overlay can be used to prevent evaporation. Excess continuous phase oil can be removed prior to heating, or left in place. The microcapsules can be resistant to coalescence and/or flocculation across a wide range of thermal and mechanical processing.

Following conversion of droplets into microcapsules, the microcapsules can be stored at about −70°, −2°, 0°, 3°, 4°, 5°, 6°, 7°, 8°, 9°, 10°, 15°, 20°, 25°, 30°, 35° or, 40° C. In some embodiments, these capsules are useful for storage or transport of partition mixtures. For example, samples can be collected at one location, partitioned into droplets containing enzymes, buffers, and/or primers or other probes, optionally one or more polymerization reactions can be performed, the partitions can then be heated to perform microencapsulation, and the microcapsules can be stored or transported for further analysis.

The microcapsule partitions can resist coalescence, particularly at high temperatures. Accordingly, the capsules can be incubated at a very high density (e.g., number of partitions per unit volume). In some embodiments, greater than 100,000, 500,000, 1,000,000, 1,500,000, 2,000,000, 2,500,000, 5,000,000, or 10,000,000 partitions can be incubated per mL. In some embodiments, the incubations occur in a single well, e.g., a well of a microtiter plate, without inter-mixing between partitions. The microcapsules can also contain other components necessary for a reaction to occur during the incubation.

In some embodiments, a sample containing one or more of the compositions described herein is partitioned into at least 500 partitions, at least 1000 partitions, at least 2000 partitions, at least 3000 partitions, at least 4000 partitions, at least 5000 partitions, at least 6000 partitions, at least 7000 partitions, at least 8000 partitions, at least 10,000 partitions, at least 15,000 partitions, at least 20,000 partitions, at least 30,000 partitions, at least 40,000 partitions, at least 50,000 partitions, at least 60,000 partitions, at least 70,000 partitions, at least 80,000 partitions, at least 90,000 partitions, at least 100,000 partitions, at least 200,000 partitions, at least 300,000 partitions, at least 400,000 partitions, at least 500,000 partitions, at least 600,000 partitions, at least 700,000 partitions, at least 800,000 partitions, at least 900,000 partitions, at least 1,000,000 partitions, at least 2,000,000 partitions, at least 3,000,000 partitions, at least 4,000,000 partitions, at least 5,000,000 partitions, at least 10,000,000 partitions, at least 20,000,000 partitions, at least partitions, at least 40,000,000 partitions, at least 50,000,000 partitions, at least partitions, at least 70,000,000 partitions, at least 80,000,000 partitions, at least partitions, at least 100,000,000 partitions, at least 150,000,000 partitions, or at least 200,000,000 partitions.

In some embodiments, a sample containing one or more of the compositions described herein is partitioned into a sufficient number of partitions such that all, substantially all, or at least a majority of partitions have no more than 1 mutant target template molecule.

In some embodiments, emulsion droplet partitions that are generated are substantially uniform in shape and/or size. For example, in some embodiments, the droplets are substantially uniform in average diameter. In some embodiments, the droplets that are generated have an average diameter of about 0.001 microns, about 0.005 microns, about 0.01 microns, about 0.05 microns, about 0.1 microns, about 0.5 microns, about 1 microns, about 5 microns, about 10 microns, about 20 microns, about 30 microns, about 40 microns, about 50 microns, about 60 microns, about 70 microns, about 80 microns, about 90 microns, about 100 microns, about 150 microns, about 200 microns, about 300 microns, about 400 microns, about 500 microns, about 600 microns, about 700 microns, about 800 microns, about 900 microns, or about 1000 microns. In some embodiments, the droplets that are generated have an average diameter of less than about 1000 microns, less than about 900 microns, less than about 800 microns, less than about 700 microns, less than about 600 microns, less than about 500 microns, less than about 400 microns, less than about 300 microns, less than about 200 microns, less than about 100 microns, less than about 50 microns, or less than about 25 microns. In some embodiments, the droplets that are generated are non-uniform in shape and/or size.

In some embodiments, the mixture partitions (e.g., emulsion droplet partitions) that are generated are substantially uniform in volume. For example, the standard deviation of mixture partition volume (e.g., droplet volume) can be less than about 1 picoliter, 5 picoliters, 10 picoliters, 100 picoliters, 1 nL, or less than about 10 nL. In some cases, the standard deviation of mixture partition volume (e.g., droplet volume) can be less than about 10-25% of the average droplet volume. In some embodiments, the mixture partitions (e.g., droplets) that are generated have an average volume of about 0.001 nL, about 0.005 nL, about 0.01 nL, about 0.02 nL, about nL, about 0.04 nL, about 0.05 nL, about 0.06 nL, about 0.07 nL, about 0.08 nL, about 0.09 nL, about 0.1 nL, about 0.2 nL, about 0.3 nL, about 0.4 nL, about 0.5 nL, about 0.6 nL, about 0.7 nL, about 0.8 nL, about 0.9 nL, about 1 nL, about 1.5 nL, about 2 nL, about 2.5 nL, about 3 nL, about 3.5 nL, about 4 nL, about 4.5 nL, about 5 nL, about 5.5 nL, about 6 nL, about 6.5 nL, about 7 nL, about 7.5 nL, about 8 nL, about 8.5 nL, about 9 nL, about 9.5 nL, about 10 nL, about 11 nL, about 12 nL, about 13 nL, about 14 nL, about 15 nL, about 16 nL, about 17 nL, about 18 nL, about 19 nL, about 20 nL, about 25 nL, about 30 nL, about 35 nL, about 40 nL, about 45 nL, or about 50 nL.

EXAMPLES

Figure 3B:
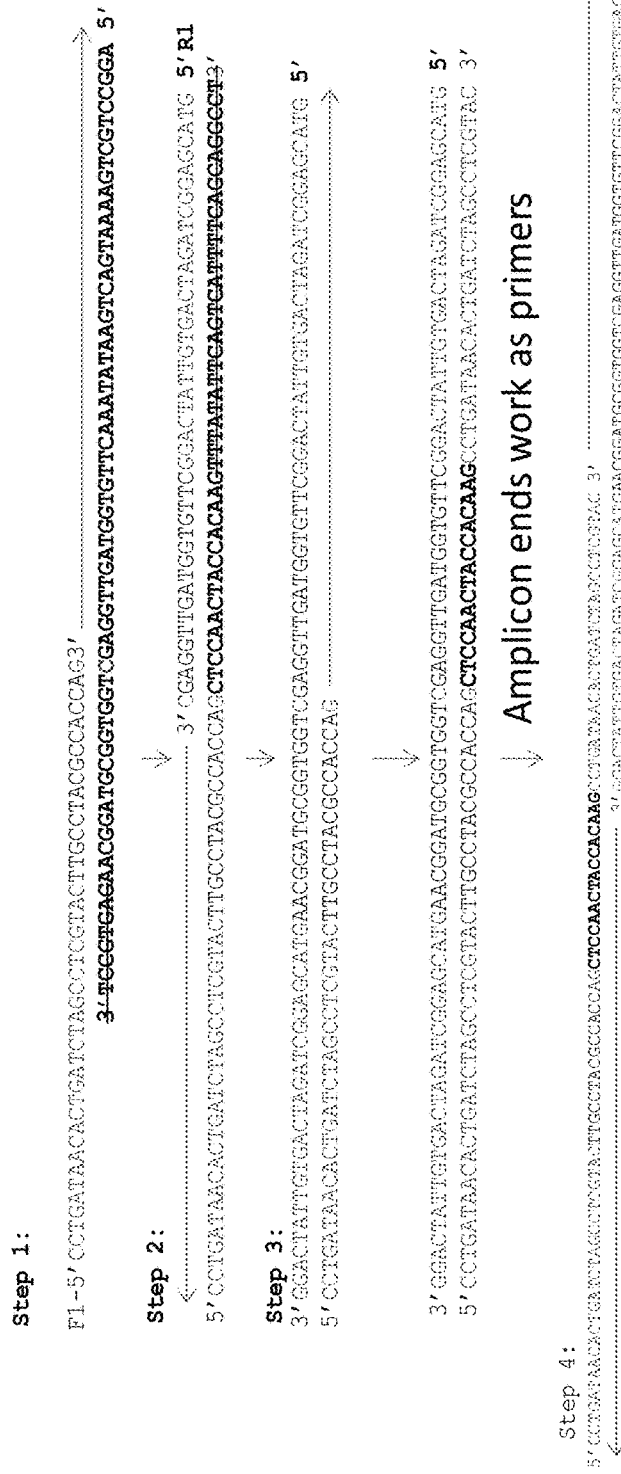

A PIK3CA mutation assay was performed on a sample to detect rare mutations. FIG. 1 illustrates exemplary primer design for wild-type and mutation-specific primers for performing split-cycle up amplification. FIG. 2 illustrates exemplary primer design for wild-type an mutation-specific primers for performing split-cycle down amplification. FIGS. 3a-b illustrate exemplary primer designs and amplification reaction schemes for performing a TAPE assay. FIG. 4 illustrates typical results expected of a rare mutation detection assay using conventional droplet digital amplification methods (Left) and a split-cycle, TAPE, or split-cycle and TAPE assay (Right) as described herein. In the conventional assay, double-negative droplets (black), single-positive mutant droplets (blue), double-positive droplets (mutant an wild-type template present in the droplet) (brown), and single-positive wild-type droplets (green) smear into each other and can be difficult to reliably distinguish at the regions bordering between two different categories of droplets. In contrast, for the split-cycle and/or TAPE assay, double-negative droplets (black), single-positive mutant droplets (blue), double-positive droplets (mutant an wild-type template present in the droplet) (brown), and single-positive wild-type droplets (green) are orthogonally situated to increase separation between droplets an increase the number of droplets that can be assigned to a specific category.

FIG. 5 illustrates results of a PIK3CA detection assay that was performed using conventional droplet digital amplification methods (Left) and a split-cycle assay (Right). The results illustrated in FIG. 5 were from a non-optimized thermal cycling protocol an reaction mixture. Further improvement can be provided by optimizing the first set of annealing and extension temperatures an second set of annealing an extension temperatures, as well as 5'-tailed an flanking primer concentrations using routine optimization methods known in the art and in view of the methods and compositions described herein. In the conventional assay, double-negative droplets (black), single-positive mutant droplets (blue), double-positive droplets (mutant an wildtype template present in the droplet) (brown), and single-positive wild-type droplets (green) smeared into each other and can be difficult to reliably distinguish at the regions bordering between two different categories of droplets. In contrast, for the split-cycle assay, double-negative droplets (black), single-positive mutant droplets (blue), double-positive droplets (mutant an wild-type template present in the droplet) (brown), and single-positive wild-type droplets (green) were orthogonally situated to increase separation between droplets an increase the number of droplets that can be assigned to a specific category, thereby improving the accuracy and sensitivity of the assay.

Although the foregoing invention has been described in some detail by way of illustration and example for purposes of clarity of understanding, one of skill in the art will appreciate that certain changes and modifications may be practiced within the scope of the appended claims. All patents, patent applications, and other publications, including GenBank Accession Numbers, cited in this application are incorporated by reference in the entirety for all purposes.

What is claimed is:

1. A plurality of mixture partitions, the individual mixture partitions comprising:
   i) a mutation-specific 5'-tailed primer pair, wherein the mutation-specific 5'-tailed primer pair hybridizes to and specifically amplifies target DNA template molecules from a nucleic acid sample that comprise a mutant target sequence, if present, wherein the primers of the mutation-specific 5'-tailed primer pair comprise:
      a) a 3' hybridization region that specifically hybridizes to the mutant target sequence; and
      b) a mutation-specific 5' tail region that does not hybridize to any nucleic acid fragments in the nucleic acid sample;
   ii) a wild-type-specific 5'-tailed primer pair, wherein the wild-type-specific 5'-tailed primer pair hybridizes to and specifically amplifies target DNA template molecules comprising a wild-type target sequence, if present, wherein the primers of the wild-type-specific 5'-tailed primer pair comprise:
      a) a 3' hybridization region that specifically hybridizes to the wild-type target sequence; and
      b) a wild-type-specific 5' tail region that does not hybridize to any nucleic acid fragments in the nucleic acid sample, wherein the wild-type-specific 5' tail region is a different sequence than the mutation-specific 5' tail region; and
   iii) a mutation-specific flanking primer pair, wherein the mutation-specific flanking primer pair hybridizes to and specifically amplifies amplicons comprising the 5' tail regions of the mutation-specific 5'-tailed primer pair, if present;
   iv) a wild-type-specific flanking primer pair, wherein the wild-type-specific flanking primer pair hybridizes to and specifically amplifies amplicons comprising the 5' tail regions of the wild-type-specific 5'-tailed primer pair, if present; and
   v) a thermostable polymerase, wherein
   at least some of the mixture partitions of the plurality of mixture partitions contain a target DNA template molecule that comprises a wild-type or mutant target sequence; and
   at least some of the mixture partitions of the plurality of mixture partitions do not contain the target DNA template molecule.

2. The plurality of mixture partitions of claim 1, wherein the mixture partitions comprise emulsion droplets.

3. The plurality of mixture partitions of claim 1, wherein at least about 10% and no more than about 90% of the plurality of mixture partitions comprise multiple target DNA template molecules.

4. The plurality of mixture partitions of claim 1 wherein the target DNA template in the mixture partitions is at an average concentration of about 1-5 copies per partition.

5. The plurality of mixture partitions of claim 1, wherein at least one of the target DNA templates in the mixture partitions comprises a mutant target sequence.

6. The plurality of mixture partitions of claim 1, wherein the plurality comprises from about 500 to about 10,000,000 mixture partitions.

7. The plurality of mixture partitions of claim 1, wherein the 3' hybridization regions of the wild-type and mutant 5'-tailed primer pairs comprise annealing temperatures to the wild-type and mutant target DNA template molecules respectively that are at least about 5° C. less than the annealing temperatures of the mutation-specific and wild-type-specific flanking primers.

8. The plurality of mixture partitions of claim 1, wherein the 3' hybridization regions of the wild-type and mutant 5'-tailed primer pairs comprise annealing temperatures to the wild-type and mutant target DNA template molecules respectively that are at least about 5° C. more than the annealing temperatures of the mutation-specific and wild-type-specific flanking primers.

9. A method for quantitating a frequency of wild-type and mutant target nucleic acid fragments in a nucleic acid sample, the method comprising:
   (a) forming a plurality of mixture partitions of claim 1;
   (b) incubating the mixture partitions under thermal cycling conditions suitable for amplification of the target DNA template molecules by a polymerase chain reaction, wherein the thermal cycling conditions comprise a first set of temperature cycles and a second set of temperature cycles, wherein the second set of temperature cycles comprises an annealing temperature that is at least 5° C. higher or lower than an annealing temperature of the first set of temperature cycles;
   (c) detecting the presence or absence of amplified target DNA template in the mixture partitions, wherein the detecting comprises, determining:
      i) a number of wild-type mixture partitions comprising amplified target DNA template consisting of wild-type target sequence;
      ii) a number of mutant mixture partitions comprising amplified target DNA template consisting of mutant target sequence; and
      iii) a number of double-positive mixture partitions comprising amplified target DNA comprising mutant and wild-type target sequence; and
   (d) determining from the number of wild-type, mutant, and double-positive mixture partitions the frequency of wild-type and mutant target nucleic acid fragments in the nucleic acid sample.

* * * * *

SEQUENCE LISTING

```
<160> NUMBER OF SEQ ID NOS: 36

<210> SEQ ID NO 1
<211> LENGTH: 68
<212> TYPE: DNA
<213> ORGANISM: Artificial Sequence
<220> FEATURE:
<223> OTHER INFORMATION: synthetic construct

<400> SEQUENCE: 1
aggcactctt gcctacgcca ccagctccaa ctaccacaag tttatattca gtcattttca     60
gcaggcct                                                              68

<210> SEQ ID NO 2
<211> LENGTH: 40
<212> TYPE: DNA
<213> ORGANISM: Artificial Sequence
<220> FEATURE:
<223> OTHER INFORMATION: synthetic construct

<400> SEQUENCE: 2
ctaggagtgg ctggaatcat ggcacgagat cctctctctg                           40

<210> SEQ ID NO 3
<211> LENGTH: 44
<212> TYPE: DNA
<213> ORGANISM: Artificial Sequence
<220> FEATURE:
<223> OTHER INFORMATION: synthetic construct

<400> SEQUENCE: 3
cctgataaca ctgatctagc ctcgtactcc tgctcagtga tttc                      44

<210> SEQ ID NO 4
<211> LENGTH: 44
<212> TYPE: DNA
<213> ORGANISM: Artificial Sequence
<220> FEATURE:
<223> OTHER INFORMATION: synthetic construct

<400> SEQUENCE: 4
caagcagaag acggcatacg agatgtcacg agatcctctc tcta                      44

<210> SEQ ID NO 5
<211> LENGTH: 45
<212> TYPE: DNA
<213> ORGANISM: Artificial Sequence
<220> FEATURE:
<223> OTHER INFORMATION: synthetic construct

<400> SEQUENCE: 5
ttactatgcc gctggtggct ctagatgctc ctgctcagtg atttt                     45

<210> SEQ ID NO 6
```

```
<211> LENGTH: 22
<212> TYPE: DNA
<213> ORGANISM: Artificial Sequence
<220> FEATURE:
<223> OTHER INFORMATION: synthetic construct

<400> SEQUENCE: 6
ctaggagtgg ctggaatcat gg                                    22

<210> SEQ ID NO 7
<211> LENGTH: 18
<212> TYPE: DNA
<213> ORGANISM: Artificial Sequence
<220> FEATURE:
<223> OTHER INFORMATION: synthetic construct

<400> SEQUENCE: 7
gattccagac actcctag                                         18

<210> SEQ ID NO 8
<211> LENGTH: 26
<212> TYPE: DNA
<213> ORGANISM: Artificial Sequence
<220> FEATURE:
<223> OTHER INFORMATION: synthetic construct

<400> SEQUENCE: 8
cctgataaca ctgatctagc ctcgta                                26

<210> SEQ ID NO 9
<211> LENGTH: 26
<212> TYPE: DNA
<213> ORGANISM: Artificial Sequence
<220> FEATURE:
<223> OTHER INFORMATION: synthetic construct

<400> SEQUENCE: 9
caagcagaag acggcatacg agatgt                                26

<210> SEQ ID NO 10
<211> LENGTH: 18
<212> TYPE: DNA
<213> ORGANISM: Artificial Sequence
<220> FEATURE:
<223> OTHER INFORMATION: synthetic construct

<400> SEQUENCE: 10
gtatgccgta ttctgctt                                         18

<210> SEQ ID NO 11
<211> LENGTH: 27
<212> TYPE: DNA
<213> ORGANISM: Artificial Sequence
<220> FEATURE:
<223> OTHER INFORMATION: synthetic construct

<400> SEQUENCE: 11
ttactatgcc gctggtggct ctagatg                               27

<210> SEQ ID NO 12
<211> LENGTH: 60
<212> TYPE: DNA
<213> ORGANISM: Artificial Sequence
<220> FEATURE:
<223> OTHER INFORMATION: synthetic construct
<220> FEATURE:
<221> NAME/KEY: misc_feature
```

```
<222> LOCATION: (1)..(10)
<223> OTHER INFORMATION: n = any nucleotide
<220> FEATURE:
<221> NAME/KEY: misc_feature
<222> LOCATION: (46)..(60)
<223> OTHER INFORMATION: n = any nucleotide

<400> SEQUENCE: 12
nnnnnnnnnn gaggacgagt cactaaacag agagaggatc tcgtgnnnnn nnnnnnnnnn       60

<210> SEQ ID NO 13
<211> LENGTH: 66
<212> TYPE: DNA
<213> ORGANISM: Artificial Sequence
<220> FEATURE:
<223> OTHER INFORMATION: synthetic construct
<220> FEATURE:
<221> NAME/KEY: misc_feature
<222> LOCATION: (1)..(13)
<223> OTHER INFORMATION: n = any nucleotide
<220> FEATURE:
<221> NAME/KEY: misc_feature
<222> LOCATION: (48)..(66)
<223> OTHER INFORMATION: n = any nucleotide

<400> SEQUENCE: 13
nnnnnnnnnn nnngaggacg agtcactaaa tagagagagg atctcgtnnn nnnnnnnnnn       60 nnnnnn                                                                  66

<210> SEQ ID NO 14
<211> LENGTH: 26
<212> TYPE: DNA
<213> ORGANISM: Artificial Sequence
<220> FEATURE:
<223> OTHER INFORMATION: synthetic construct

<400> SEQUENCE: 14
gaatcatggc ttgtggtagt tggagc                                            26

<210> SEQ ID NO 15
<211> LENGTH: 28
<212> TYPE: DNA
<213> ORGANISM: Artificial Sequence
<220> FEATURE:
<223> OTHER INFORMATION: synthetic construct

<400> SEQUENCE: 15
ctagcctcgt acttgcctac gccaccag                                          28

<210> SEQ ID NO 16
<211> LENGTH: 29
<212> TYPE: DNA
<213> ORGANISM: Artificial Sequence
<220> FEATURE:
<223> OTHER INFORMATION: synthetic construct

<400> SEQUENCE: 16
catacgagat gtcttgtggt agttggagg                                         29

<210> SEQ ID NO 17
<211> LENGTH: 23
<212> TYPE: DNA
<213> ORGANISM: Artificial Sequence
<220> FEATURE:
<223> OTHER INFORMATION: synthetic construct

<400> SEQUENCE: 17
```
ctctagatgg cctacgccac cac    23

<210> SEQ ID NO 18
<211> LENGTH: 9
<212> TYPE: DNA
<213> ORGANISM: Artificial Sequence
<220> FEATURE:
<223> OTHER INFORMATION: synthetic construct

<400> SEQUENCE: 18 gaatcatgg    9

<210> SEQ ID NO 19
<211> LENGTH: 11
<212> TYPE: DNA
<213> ORGANISM: Artificial Sequence
<220> FEATURE:
<223> OTHER INFORMATION: synthetic construct

<400> SEQUENCE: 19
ctagcctcgt a    11

<210> SEQ ID NO 20
<211> LENGTH: 12
<212> TYPE: DNA
<213> ORGANISM: Artificial Sequence
<220> FEATURE:
<223> OTHER INFORMATION: synthetic construct

<400> SEQUENCE: 20
catacgagat gt    12

<210> SEQ ID NO 21
<211> LENGTH: 10
<212> TYPE: DNA
<213> ORGANISM: Artificial Sequence
<220> FEATURE:
<223> OTHER INFORMATION: synthetic construct

<400> SEQUENCE: 21
gctctagatg    10

<210> SEQ ID NO 22
<211> LENGTH: 15
<212> TYPE: DNA
<213> ORGANISM: Artificial Sequence
<220> FEATURE:
<223> OTHER INFORMATION: synthetic construct

<400> SEQUENCE: 22
ttggagctgg tggcg    15

<210> SEQ ID NO 23
<211> LENGTH: 16
<212> TYPE: DNA
<213> ORGANISM: Artificial Sequence
<220> FEATURE:
<223> OTHER INFORMATION: synthetic construct

<400> SEQUENCE: 23
gtagttggag gtggtg    16

<210> SEQ ID NO 24
<211> LENGTH: 68
<212> TYPE: DNA
<213> ORGANISM: Artificial Sequence

```
<220> FEATURE:
<223> OTHER INFORMATION: synthetic construct

<400> SEQUENCE: 24
aggcactctt gcctacgcca ccacctccaa ctaccacaag tttatattca gtcattttca      60
gcaggcct                                                               68

<210> SEQ ID NO 25
<211> LENGTH: 37
<212> TYPE: DNA
<213> ORGANISM: Artificial Sequence
<220> FEATURE:
<223> OTHER INFORMATION: synthetic construct

<400> SEQUENCE: 25
cctgataaca ctgatctagc ctcgtacttg cctacgc                               37

<210> SEQ ID NO 26
<211> LENGTH: 37
<212> TYPE: DNA
<213> ORGANISM: Artificial Sequence
<220> FEATURE:
<223> OTHER INFORMATION: synthetic construct

<400> SEQUENCE: 26
gtacgaggct agatcatgtt atcaggcttg tggtagt                               37

<210> SEQ ID NO 27
<211> LENGTH: 17
<212> TYPE: DNA
<213> ORGANISM: Artificial Sequence
<220> FEATURE:
<223> OTHER INFORMATION: synthetic construct

<400> SEQUENCE: 27
caccagctcc aactacc                                                     17

<210> SEQ ID NO 28
<211> LENGTH: 68
<212> TYPE: DNA
<213> ORGANISM: Artificial Sequence
<220> FEATURE:
<223> OTHER INFORMATION: synthetic construct

<400> SEQUENCE: 28
aggcctgctg aaaatgactg aatataaact tgtggtagtt ggagctggtg gcgtaggcaa      60
gagtgcct                                                               68

<210> SEQ ID NO 29
<211> LENGTH: 38
<212> TYPE: DNA
<213> ORGANISM: Artificial Sequence
<220> FEATURE:
<223> OTHER INFORMATION: synthetic construct

<400> SEQUENCE: 29
gtacgaggct agatcagtgt tatcaggctt gtggtagt                              38

<210> SEQ ID NO 30
<211> LENGTH: 87
<212> TYPE: DNA
<213> ORGANISM: Artificial Sequence
<220> FEATURE:
<223> OTHER INFORMATION: synthetic construct
```

<400> SEQUENCE: 30
cctgataaca ctgatctagc ctcgtacttg cctacgccac cagctccaac taccacaagt    60
ttatattcag tcattttcag caggcct                                        87

<210> SEQ ID NO 31
<211> LENGTH: 86
<212> TYPE: DNA
<213> ORGANISM: Artificial Sequence
<220> FEATURE:
<223> OTHER INFORMATION: synthetic construct

<400> SEQUENCE: 31
gtacgaggct agatcagtgt tatcaggctt gtggtagttg gagctggtgg cgtaggcaag    60
tacgaggcta gatcagtgtt atcagg                                         86

<210> SEQ ID NO 32
<211> LENGTH: 86
<212> TYPE: DNA
<213> ORGANISM: Artificial Sequence
<220> FEATURE:
<223> OTHER INFORMATION: synthetic construct

<400> SEQUENCE: 32
cctgataaca ctgatctagc ctcgtacttg cctacgccac cagctccaac taccacaagc    60
ctgataacac tgatctagcc tcgtac                                         86

<210> SEQ ID NO 33
<211> LENGTH: 43
<212> TYPE: DNA
<213> ORGANISM: Artificial Sequence
<220> FEATURE:
<223> OTHER INFORMATION: synthetic construct

<400> SEQUENCE: 33
cctgataaca ctgatctagc ctcgtacttg cctacgccac cag                      43

<210> SEQ ID NO 34
<211> LENGTH: 44
<212> TYPE: DNA
<213> ORGANISM: Artificial Sequence
<220> FEATURE:
<223> OTHER INFORMATION: synthetic construct

<400> SEQUENCE: 34
gtacgaggct agatcagtgt tatcaggctt gtggtagttg gagc                     44

<210> SEQ ID NO 35
<211> LENGTH: 10
<212> TYPE: DNA
<213> ORGANISM: Artificial Sequence
<220> FEATURE:
<223> OTHER INFORMATION: synthetic construct

<400> SEQUENCE: 35
ggactattgt                                                           10

```
<210> SEQ ID NO 36
<211> LENGTH: 43
<212> TYPE: DNA
<213> ORGANISM: Artificial Sequence
<220> FEATURE:
<223> OTHER INFORMATION: synthetic construct

<400> SEQUENCE: 36
gtacgaggct agatcatgtt atcaggcttg tggtagttgg agc                43
```